United States Patent
Wolfinbarger, Jr.

(10) Patent No.: US 6,189,537 B1
(45) Date of Patent: Feb. 20, 2001

(54) PROCESS FOR PRODUCING OSTEOINDUCTIVE BONE, AND OSTEOINDUCTIVE BONE PRODUCED THEREBY

(75) Inventor: Lloyd Wolfinbarger, Jr., Norfolk, VA (US)

(73) Assignee: LifeNet

(*) Notice: Under 35 U.S.C. 154(b), the term of this patent shall be extended for 0 days.

(21) Appl. No.: 08/706,707

(22) Filed: Sep. 6, 1996

(51) Int. Cl.[7] .................................................. A61B 19/00
(52) U.S. Cl. ............................ 128/898; 623/16; 623/11; 623/66; 623/901
(58) Field of Search ................................ 128/898; 514/21, 514/801; 424/549; 623/1, 11, 16, 66, 18, 901; 606/76, 213

(56) References Cited

U.S. PATENT DOCUMENTS

| | | | |
|---|---|---|---|
| 4,485,097 | * 11/1984 | Bell ....................................... 623/11 X |
| 4,516,276 | * 5/1985 | Mittelmeier et al. ............. 606/213 X |
| 5,275,954 | * 1/1994 | Wolfinbarger et al. ........... 424/549 X |
| 5,531,791 | * 7/1996 | Wolfinbarger, Jr. ...................... 623/16 |

* cited by examiner

Primary Examiner—Mickey Yu
Assistant Examiner—Kelly O'Hara
(74) Attorney, Agent, or Firm—Susanne M. Hopkins

(57) ABSTRACT

The invention produces osteoinductive bone using a controlled-flow apparatus. The apparatus allows for the controlled extraction of undesirable constituents from a body tissue. The invention provides for the demineralization of ground bone particles or pieces of cancellous or cortical bone which permits the controlled and reproducible demineralization of bone to produce bone which is maximally osteoinductive. It has been demonstrated that ground cadaveric bone which is demineralized to a residual calcium level approximating 2% by dry weight of bone is optimally osteoinductive as assayed using in vivo and in vitro assays of osteoinductivity. The controlled-flow apparatus includes one or more solution containers which supply solutions to be pumped into one or more vessels filled with tissue samples to be extracted. Solvent outflowing from the vessels can be monitored for pH, calcium ion concentration or conductivity as a basis for determining when extraction is complete. Using the invention, a linear relationship has been shown to exist between eluent pH and percent residual calcium in the bone being demineralized. Thus, the invention permits the reproducible demineralization of bone which is optimally osteoinductive. The invention also corrects the percent residual calcium in bone which is overly demineralized, returning it to a state of being optimally osteoinductive.

17 Claims, 19 Drawing Sheets

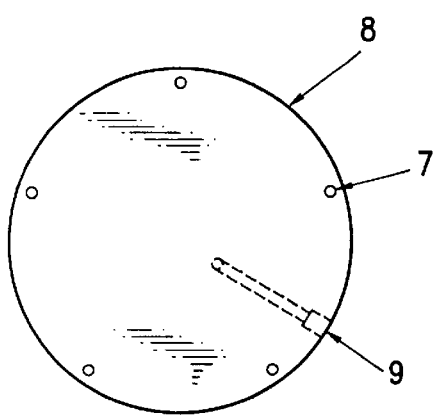
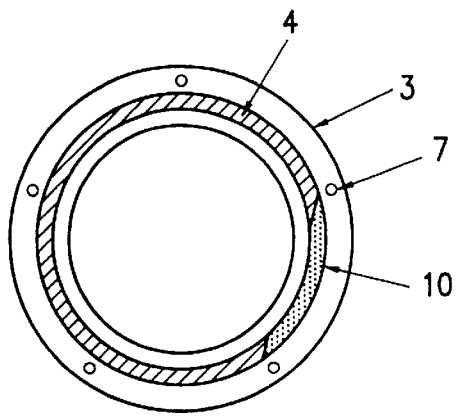
FIG. 3　　　　　FIG. 4
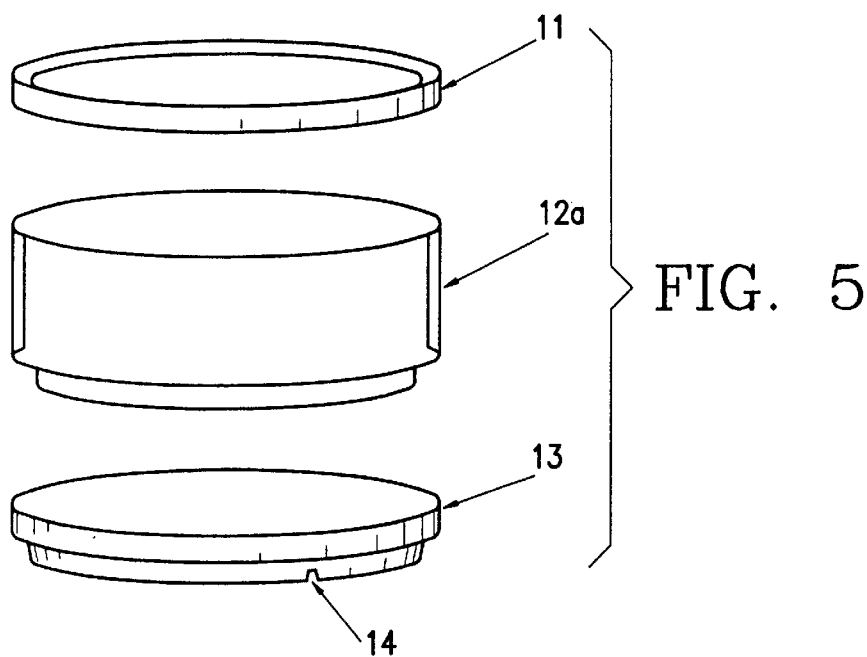
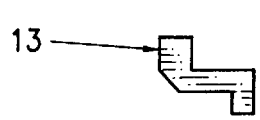
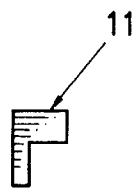
FIG. 6　　　　　FIG. 7

PROCESS FOR PRODUCING OSTEOINDUCTIVE BONE, AND OSTEOINDUCTIVE BONE PRODUCED THEREBY

FIELD OF THE INVENTION

The invention concerns a process and apparatus for producing osteoinductive bone and osteoinductive bone produced thereby. The present inventor has surprisingly discovered that ground bone can be optimally demineralized to produce maximally osteoinductive bone and that bone is optimally demineralized when it is demineralized to the point of containing approximately 2 wt % residual calcium is maximally osteoinductive. The invention is also directed to a controlled-flow apparatus for extracting undesirable constituents from tissue. The present controlled-flow apparatus is used with the present process to produce osteoinductive bone.

BACKGROUND OF THE INVENTION

It is known that implantation of acid demineralized bone (DMB) in the form of a powder in extraskeletal sites stimulates new bone formation. Various research groups (Syftestad, 1982; Urist et al., 1967; Urist and Strates, 1979; Urist and Strates, 1971; Urist et al., 1983) have suggested that a noncollagenous protein(s) present in demineralized bone has the ability to induce new bone formation when present within the implanted bone matrix.

Procedures presently utilized to demineralize ground bone fragments involve the use of ethanol to remove lipids and hydrochloric acid to remove the mineral components of bone.

It is also known to treat bones and bone particles to render them biocompatible so that they can be implanted in living animal and human bodies without being rejected. Included among the known methods for treating bone is the dilapidation of bone using ethanol or chloroform. It is further known to demineralize bone matrix with an inorganic acid such as hydrochloric acid.

Although it is well known to defat and demineralize bone for implantation purposes, known methods of demineralizing and removing lipids have been extremely tedious, labor intensive, and slow. Furthermore, an excessive amount of handling and/or exposure of the bone to non-sterile conditions has been necessary during the various phases of processing.

SUMMARY OF THE INVENTION

The present invention is based on the present inventors surprising discovery that bone can be over and under demineralized and that this alters the osteoinductivity, as one function of the demineralized bone material, of the demineralized bone. It has been presently shown that a linear relationship exists between the pH of the eluent demineralization solution and the wt % residual calcium. Thus, it is one object of the present invention to provide controlled-flow apparatus for extracting undesirable constituents from tissue, including use with the present dilapidation and demineralization process for producing osteoinductive bone.

Included in this object is the method to restore overly demineralized bone to a state of being maximally osteoinductive.

It is further object of the present invention to provide an apparatus and method for the simultaneous dilapidation and demineralization of multiple bone samples.

It is a further object of the present invention to provide an apparatus and process for dilapidation and demineralization of bone samples which is less tedious and labor intensive than prior art methods and which is less likely to produce bone which is microbiologically contaminated following the dilapidation and demineralization process.

It is a further object of the present invention to provide a method of reprecipitating calcium phosphate in overly demineralized bone to restore it to a state of being maximally osteoinductive.

Other objects and advantages of the present invention and advantages of other features thereof will become apparent as the description proceeds herein.

Included in the description are in vivo and in vitro assays used in assessing the osteoinductive potential of demineralized bone and that demineralized bone particles of particular particle size ranges and wt % residual calcium are maximally osteoinductive. The desired wt % residual calcium levels are readily achieved using the apparatus and process described herein.

The apparatus for processing tissue comprises at least one vessel for containing the solid matter where each vessel has an upper end and lower end. Each lower end has an inlet port and each upper end has an eluent drain. Each vessel is adapted to contain solid matter during the extent of processing. The apparatus may further include a driving mechanism for conducting the solvent flow of through each vessel, which is preferably at least one peristaltic pump and solvent reservoirs for holding the solvents which are to be conducted through the vessels. Eluent solution can be monitored for change in pH, calcium ion concentration, or conductivity, through use of a pH meter or calcium specific electrode attached to an ion meter.

Preferred solid materials to be processed in the apparatus include any body tissue preferably particulate bone, cancellous bone, and/or strips or cubes of cortical bone. The entire apparatus can be contained within a controlled environment chamber which is capable of maintaining the apparatus at a processing temperature range of 4° C. to 42° C., preferably 15° C. to 30° C., and most preferably 20° C. to 25° C.

The invention further includes a method involving the soaking of overly demineralized bone in concentrated solutions of calcium phosphate made sufficiently acid to dissolve the calcium phosphate followed by reprecipitation of calcium phosphate onto and within the collagen and noncollagen matrix of the bone by increasing the pH of the solution to the point that the calcium phosphate is no longer soluble.

The invention also includes in vitro and in vivo assays for assessing the osteoinductive potential of the produced osteoinductive bone. The in vivo assay includes an athymic "nude" mouse system where the 5 to 10 mg of ground osteoinductive bone is implanted in muscle pouches in the gluteal region. The implanted material(s) are explanted, optimally after 4 weeks, cleaned of excess soft tissue and solubilized in dilute hydrochloric acid prior to determination of calcium content using any available assay, for example atomic absorption. The in vitro assay includes a tissue culture based assay where periosteum-derived cells growing in culture are exposed to 10 to 20 mg of demineralized bone per T-25 tissue culture flask containing 5 to 15 mls of an appropriate medium. After about 4 to 5 days in culture, the cells are washed and harvested and assayed for levels of alkaline phosphatase using commercially available kits (see for example Sigma Chemical Company, St. Louis, Miss.). The Atomic Absorption Assay (AA) is well know to those of ordinary skill in the art with this assay. The Arzenazo III assay involves the binding of this dye to calcium ion with a shift in absorption characteristics where the absorbance can be monitored using a spectrophotometer and absorbance is a linear function of calcium ion concentration. The alkaline phosphatase (Apase) assay involves the conversion of para-nitrophenolphosphate (PNPP) to para-nitrophenol (PNP) by the enzyme alkaline phosphate at alkaline pH. The para-nitrophenol exhibits a unique absorbance and the amount of PNP formed per unit time interval can be quantitated by comparison of changes in absorbance to a standard curve of PNP. Both assays are well know in the art and both are commercially available assays from, for example, Sigma Chemical Company, St. Louis, Miss.

BRIEF DESCRIPTION OF THE FIGURES

The present invention is further explained in the description which follows with reference to the figures and drawings, by way of non-limiting examples, various embodiments of the invention, with like reference legends representing similarly collected data throughout the several figures and drawings.

FIG. 3 illustrates a top view of cover 8 of the main body of the present controlled-flow apparatus.

FIG. 4 illustrates a tip view of the present flanged top edge 3 of the main vessel 1.

FIG. 5 illustrates a side view of the present large inner member.

FIG. 6 illustrates a cross section of bottom secure ring 13 of the large or small inner member.

FIG. 7 illustrates a cross section of the top secure ring 11 of the large or small inner member.

DESCRIPTION OF THE PREFERRED EMBODIMENTS

I. Definitions

Figure 1:
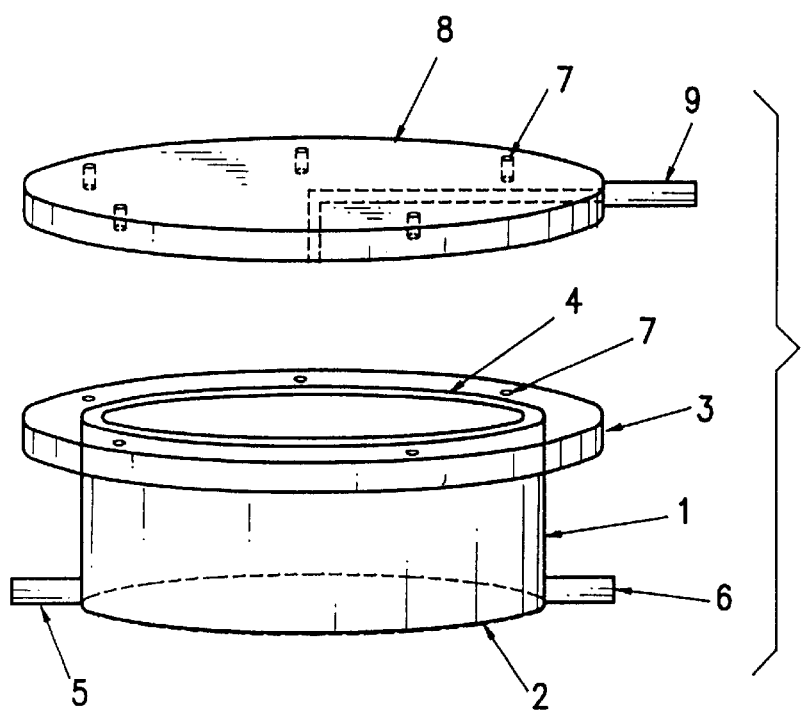
FIG. 1 illustrates a plan view of the main body portion of the present controlled-flow apparatus having cylindrically shaped inlet port 5, drain port 6 and eluent drain 9.

The below definitions serve to provide a clear and consistent understanding of the specification and claims, including the scope to be given such terms.

Acid

By the terms "acid" is intended any acid capable of demineralizing bone most preferably, hydrochloric acid. Other suitable acids involved: formic acid<acetic acid<citric acid<propionic acid (organic acid)("<" indicates that the acid to the left of this sign is more preferred than that acid to the right of this sign.), hydrochloric acid<phosphoric acid(inorganic acid); chelators such as ethylenedediamine-tetracetic acid (EDTA) (or analogues of this chelator such as EGTA), citric acid, succinic acid, heparin, etc. can be used to chelate (bind) calcium which aids in the demineralization of bone by both organic and inorganic acids.

Allowash™ Solution

By the term "Allowash™ solution" is intended those detergent compositions disclosed in co-pending U.S. patent application Ser. No. 08/620,856 incorporated herein by reference. Examples of suitable Allowash™ compositions include: a cleaning composition containing essentially about 0.06 wt % polyoxyethylene-4-lauryl ether, about 0.02 wt % poly (ethylene glycol)-p-nonyl-phenyl-ether; about 0.02 wt % octylphenol-ethyleneoxide and endotoxin free deionized/distilled water.

Body Tissue

By the term "body tissue" it is intended for the purposes of the present invention any tissue suitable for transplantation into a human, which tissue contains one or more constituents whose presence in that particular tissue to be transplanted is undesirable, for example, blood cells; bacteria; fungi; viruses; in the case of bone tissue, bone marrow elements which include blood cells, for example, and lipid. Suitable body tissue for use with the present procedure and apparatus include, but are not limited to: musculoskeletal tissue and cardiovascular tissue including but not limited to bone tissue, tendons, ligaments, arteries and veins, and heart valves.

Bone

By the term "bone" is intended for the purposes of the present invention any bone from any source preferably human cadaveric bone in a form capable of being demineralized for example, ground bone; particulate bone (i.e., dental bone) preferably in the particle size range of 250µ to 710µ; bone chips; and cancellous and/or cortical bone strips and/or cubes.

Bone Marrow Elements

By the term "bone marrow elements" is intended for the purpose of the present invention the highly cellular hematopoietic connective tissue filling the medullary cavities and spongy epiphyses of bones which may harbor bacterial and/or viral particles and/or fungal particles, and includes, for example blood and lipid.

Cleaning Container

By the term "cleaning container" is intended for the purposes of the present invention any rigid or deformable container or reservoir of a size sufficient to contain the solvent or solvents used for processing a particular tissue.

Detergent

By the term "detergent" is intended any agent which through a surface action that depends on it possessing both hydrophilic and hydrophobic properties and/or exerts oil-dissolving (cleansing) and/or antibacterial and/or antiviral effects, and can include but is not limited to: anionic detergents, cationic detergents, acridine derivatives, long-chain aliphatic basis or acids, also including compositions such as "Allowash™ solution."

Disinfectant

By the term "disinfectant" is intended one or more agents which remove or inactivate/destroy any infectious material potentially present in the bone marrow of a bone graft, for example, such materials including but not limited to: bacteria, virus, and/or fungi; with such decontaminating agents including, for example, but not limited to one or more of the following: an antibacterial agent; an antiviral agent; antimycotic agent; an alcohol for example, methyl, ethyl, propyl, isopropyl, butyl, and/or t-butyl; trisodium phosphate; sodium hydroxide; hydrogen peroxide; and/or any detergent.

Flow

By the term "flow" is intended the movement of a fluid, specifically the volume of fluid passing a given point, per unit time. Suitable flow rates for the current application are 5 ml/min to 100 ml/min; preferably 10 ml/min to 50 ml/min; more preferably 15 ml/min to 30 ml/min; and most preferably 20 ml/min.

Lipid

By the term "lipid" is intended the fat-soluble constituents of bone marrow, for example fatty acids, glycerides, and phospholipids.

Solvent

By the term "solvent" is intended for the purposes of the present invention, a liquid cleaning composition capable of: facilitating the solubilization of lipid, facilitating bone marrow removal, inactivating viral and/or bacterial particles, and/or disrupting cell membranes, and/or demineralizing bone, which may contain, but is not limited to, one or more of the following: sterile water; saline; a detergent; a disinfectant; an acid; an alcohol, for example, ethanol and/or isopropanol; solvents; a combination of solutes desired to facilitate solubilization of bone marrow, for example, Allowash™ solution disclosed in co-pending application Ser. No. 08/620,856 herein incorporated by a reference; a chelating agent; a bacteriocidal agent; an antimycotic agent; sodium hydroxide or similar strong base; organic and/or inorganic acid known and used in the art for the demineralization of bone including, for example, hydrochloric acid; and/or hydrogen peroxide. Known lipophilic solvents include, for example, ethanol and chloroform.

Undesirable constituents

By the term "undesirable constituents" is intended for the purposes of the present invention any constituents normally associated with a particular tissue whose presence in that tissue to be transplanted is undesirable, for example, blood cells; bacteria; fungi; viruses; in the case of bone, bone marrow elements including lipid and blood, and any other constituents normally associated with bone marrow as well as any bacterial, viral or fungal contamination associated with the bone and/or bone marrow elements.

II. Detailed Description of the Figures

The present controlled-flow apparatus is used for the controlled removal of undesirable constituents from a body tissue, for example, for the controlled demineralization of bone tissue using the present demineralization process to produce optimally osteoinductive bone tissue suitable for transplantation in humans. The present apparatus consists of a main body and an inner member. The inner member is either a large inner member or a small inner member apparatus. The large inner member is used in the main body of the present controlled-flow apparatus when large quantities of tissue are being processed, for example, in the case of bone 300 g wet weight or more. The small inner member is used with a spacer when a smaller quantity of tissue is being processed, for example, in the case of bone 300 g wet weight or less. While it is not critical that the small inner member be used for processing small quantities of tissue, use of the small inner member allows for greater efficiency in that the amount of solvent used in the process is minimized.

Referring now to the figures and drawings in detail, FIG. 1 illustrates the main body portion of the present controlled-flow apparatus for the controlled extraction of tissue, for example, for the controlled demineralization and dilapidation of bone tissue samples. FIG. 1 illustrates the generally cylindrical main vessel 1 having a closed bottom 2 and a flanged top edge 3. The main vessel may be generally cylindrical, perfectly cylindrical or oval.

The main vessel 1 contains at least one and preferably at least two ports. During demineralization solvent enters the main vessel 1 through inlet port 5. The other port is drain port 6 which allows for quick removal of the solvent once the undesirable constituents of the tissue have been extracted to a desired level, for example, in the case of bone, once the bone tissue has reached a preferred wt % residual calcium level.

The main body of the preferred embodiment of the present controlled-flow apparatus also contains a cover 8 which during processing is fit over the top flanged edge 3 of the main vessel 1. Cover 8 additionally contains a eluent drain 9 and may contain two or more bore holes 7 for fitting the cover 8 onto the top flanged edge 3 of the main vessel 1. Likewise, the top flanged edge 3 of the main vessel 1 may also contains two or more bore holes 7. In order to provide a fluid seal which withstands minimal pressure for example, pressure in the range of from 1.0 to 1.5 atm; more preferably 1.0 to <1.5 atm; and most preferably 1.0 atm top flanged edge 3 of the main vessel 1 is provided with an annular groove into which an O-ring is fit. Once the O-ring is placed within the groove on the top flanged edge 3, the cover 8 is fitted over the top flanged edge 3 with the bore holes 7 aligned. Appropriately sized fastening means, for example, bolts and nuts are then used to tighten down the cover 8 onto the top flanged edge 3 of the main vessel 1.

Figure 2:
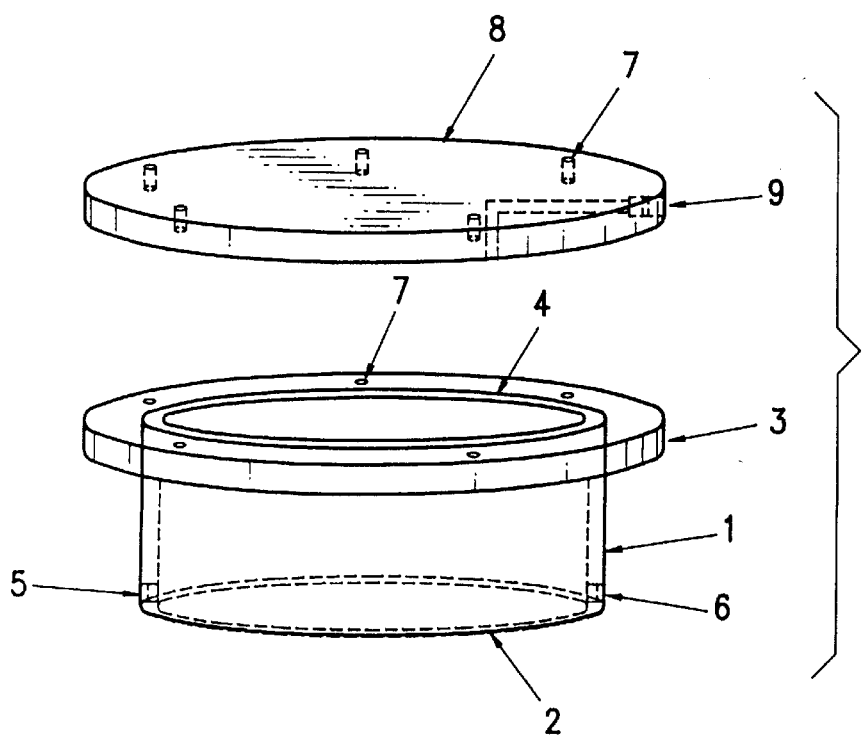
FIG. 2 illustrates a plan view of the main body of the present controlled-flow apparatus having threaded inlet port 5, threaded drain port 6, and threaded eluent drain 9.

During processing, solvent enters the main body of the present controlled-flow apparatus through inlet port 5 and exits the main body of the controlled-flow apparatus through eluent drain 9. Inlet port 5, drain port 6, and eluent drain 9, may be as shown in FIG. 1 or as shown in FIG. 2. In FIG. 1, these ports consist of a generally cylindrical tube-like member which is an integral part of, for example, in the case of inlet port 5 and drain port 6 of the main vessel 1. Alternatively, these tube-like members may be formed of a different material and fitted into a bore through a bottom portion of a sidewall of main vessel 1. This separate tube-like member may consist of the same material as the main body of the controlled-flow apparatus or a different material, provided that all materials used in the apparatus are stable in the presence of an acidic solvent. When using ports as illustrated in FIG. 1, appropriately sized tubing may be slipped over, for example, the inlet port 5 and the drain port 6, as well as the eluent drain 9, or the inlet port 5, drain port 6, and eluent drain 9, may be formed so as to have internal or external threads so that an adapter can be screwed into or over any and/or all of inlet port 5, drain port 6, or eluent drain 9. An adapter can be used, for example, one end of the adapter can be threaded so that it can be screwed into one or more of the ports, while the other end of the adapter can be configured so as to allow attachment of appropriately sized tubing. Alternatively, an adapter which provides a frictional fit between the adapter and the port, or tubing having an appropriately rigidity can itself be used to provide a frictional fit between the port and the tubing either by fitting the tubing inside of the port or over the outside of the port.

FIG. 2 illustrates inlet port 5, drain port 6, and eluent drain 9 as being threaded bore holes in the case of inlet port 5 and drain port 6, through the bottom portion of the sidewall of the main vessel 1. In the case of eluent drain 9, only a portion of the bore is threaded.

FIG. 3 illustrates a top view of the cover 8 having a plurality of bore holes 7 and eluent drain 9.

FIG. 4 illustrates a tip view of the top flanged edge 3 of the main vessel 1 having a plurality of bore holes 7, a groove 4 for containing an O-ring 10. Groove 4, O-ring 10, and bore holes 7, are not critical to the present controlled-flow apparatus. It is critical that a fluid-tight seal able to withstand minimal pressure be provided between the main vessel 1 and the cover 8 containing the eluent drain 9. Other means of accomplishing a fluid-tight seal are contemplated by the present invention including, for example, the use of a gasket consisting of a stable material appropriate for the solvent being used which material can readily be selected by one of ordinary skill in the art, where the gasket is placed between the top flanged edge 3 of the main vessel 1 and where the cover 8 is fitted tightly against the gasket and top flanged edge 3 using for example pressure, for example, pressure exerted using, for example, a mechanical clamp, or by providing the cover 8 with an annular lip threaded so as to screw onto main vessel 1 also being appropriately threaded at its top edge.

FIG. 5 illustrates the large inner member for use with the present controlled-flow apparatus when the amount of tissue being processed is large, for example, in the case of bone 300 g wet weight or more. This large inner member is preferably generally cylindrical but may be of a different shape including for example, oval. The large inner member contains a generally cylindrical top secure ring 11, a generally cylindrical tall inner vessel 12a, and a generally cylindrical bottom secure ring 13, having at its bottom edge, one or more notches 14 of a size appropriate to allow tubing to run, for example, from the inlet port 5 through the notch 14 and into the inner vessel so as to allow solvent to enter the inner vessel of the main body of the present controlled-flow apparatus. An additional notch may be provided and appropriately located so as to allow tubing to run from the bottom secure ring 13 of the inner vessel through the drain port 6, and directed to waste so as to allow for quick removal of the solvent. The inner vessel 12 is generally cylindrical having both an open top end and an open bottom end. Likewise, the bottom secure ring 13 has an open top and an open bottom end as does top secure ring 11.

FIG. 6 illustrates a preferred cross section view of the bottom secure ring 13.

FIG. 7 illustrates a preferred cross section view of the top secure ring 11.

The bottom edge of the top secure ring 11 is fitted onto the top edge of the inner vessel 12; the bottom edge of inner vessel 12 is fitted into bottom secure ring 13. The exact shape and cross sections of the top secure ring, the bottom edge of the inner vessel, and the bottom secure ring, are not critical. It is only critical that these members fit together as described and provide a fluid-tight seal. This may accomplished as illustrated and may optionally include the use of a gasket, or an O-ring fitted into appropriately configured grooves provided on any one or more edges of the members, for example, provided on the bottom edge of inner vessel 12, provided on the internal surface of the bottom edge of bottom secure ring 13, or provided on an internal surface of the top edge of top secure ring 11. Alternatively, top secure ring 11 and bottom secure ring 13 may be frictionally fit onto inner vessel 12 or may be threaded so as to fit onto inner vessel 12 when inner vessel 12 is also provided with appropriate threading at its bottom and/or its top edge.

Figure 8:
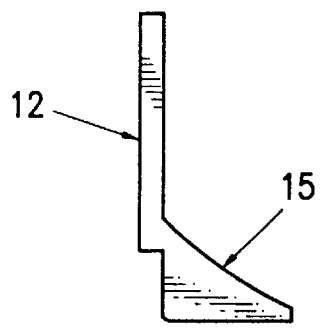
FIG. 8 illustrates a cross section of either the tall or short inner vessel 12a or 12b of the large or small inner member having a straight angled surface 15.

FIG. 8 illustrates a cross section view of inner vessel 12 having a straight angled surface 15.

Figure 9:
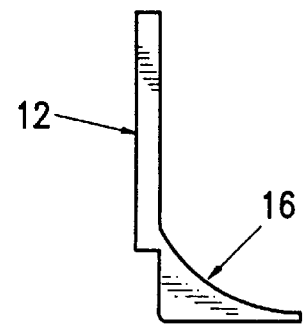
FIG. 9 illustrates either the tall 12a or short 12b inner vessel of the either the large or small inner member having a concave surface 16.

FIG. 9 illustrates a cross section view of inner vessel 12 having a concave inner surface 16.

Figure 10:
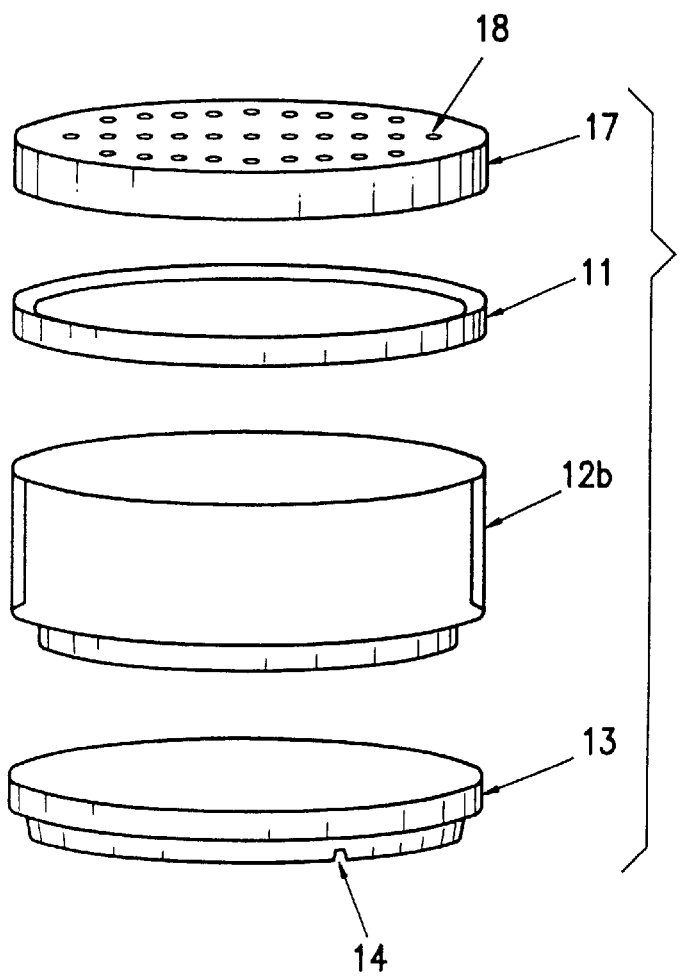
FIG. 10 illustrates the small inner member for use with the main body of the present controlled-flow apparatus.

FIG. 10 illustrates the present small inner member for use with the main body of the present controlled-flow apparatus when the amount of bone tissue to be processed is small, for example, in the case of particulate bone 300 g wet weight or less. The small inner member consists of a generally cylindrical top secure ring 11, a generally cylindrical short inner vessel 12b, and a generally cylindrical bottom secure ring 13 having one or more notches 14 provided on its bottom edge. Top secure ring 11 and bottom secure ring 13 are identical to top secure ring 11 and bottom secure ring 13 used in conjunction with the large inner member. Short inner vessel 12b is similar to tall inner vessel 12a used with the large inner member except that the height of this inner vessel 12*b* is less than the height of the tall inner vessel 12*a*. Additionally, the small inner member is provided with a generally cylindrical spacer 17 having a plurality of bore holes 18. The exact number of bore holes provided in the spacer 17 is not critical so long a sufficient number of bore holes are provided so that fluid flow is not impeded. Spacer 17 serves to prevent the small inner vessel 12*b* from floating up in the main body of the present controlled-flow apparatus during the present process. The small inner member is preferably used when the amount of tissue to processed is small. Use of the small inner member conserves solvent and allows for a more efficient processing of the tissue.

Figure 11:
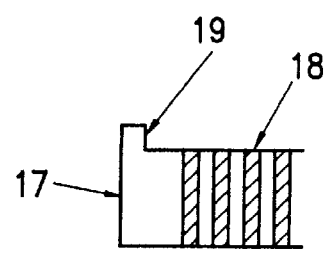
FIG. 11 illustrates a cross section of spacer ring 17 having annular lip 19 and bore holes 18.

FIG. 11 illustrates a cross sectional view of spacer 17, where the spacer 17 is provided with a plurality of bore holes 18, and an annular top lip 19.

To prepare the controlled-flow apparatus for extracting a body tissue, for example, demineralizing bone tissue, based on the amount of bone tissue to processed one of ordinary skill in the art can readily select the appropriate inner member for use with the main body of the present controlled-flow apparatus. Upon selection of the appropriate inner member, for example, when the amount of bone tissue to be processed is small, the small inner member is selected.

Figure 12:
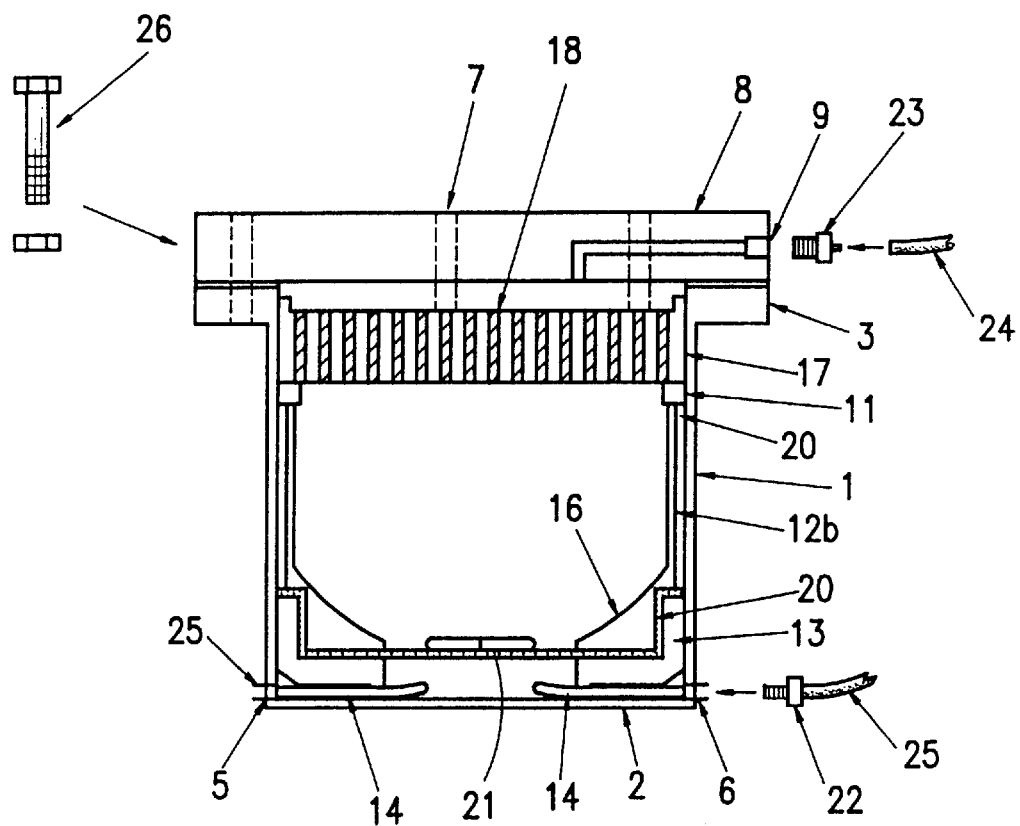
FIG. 12 illustrates a cross section of the present controlled-flow apparatus using the small inner member.

FIG. 12 illustrates the present controlled-flow apparatus containing the main body of the apparatus and the small inner member for use in processing a small quantity of, for example, bone tissue. The small inner member consists of short inner vessel 12*b* fitted into bottom secure ring 13 having an appropriately sized piece of filter material 20 is press fitted between the short inner vessel 12*b* and bottom secure ring 13. More specifically, the bottom secure ring is press fitted onto the bottom end of the short inner vessel. Once the bottom secure ring is press fitted onto the bottom of the vessel, which has the filter material 20 at its bottom end, the bone tissue to be processed is placed into the vessel preferably with a magnetic stir bar 21. After the bone tissue is placed in the vessel, the top end of the short inner vessel is covered with an additional piece of appropriately sized filter material 20 and the top secure ring 11 is then press fitted over the top edge of the short inner vessel provided with the filter material 20. Cover 8 is fitted on to top flanged edge 3 and secured using bolts and nuts 26 through bore holes 7.

During processing, for example, of particulate bone using an acidic solvent, the solvent flows from a container through appropriately sized and acid stable tubing, for example, Masterflex©, number 6424-14. Along the length of the tubing, a valve may be installed so as to allow, stop or regulate solvent flow. The tubing enters the main vessel 1 of the main body through inlet port 5. Inlet port 5 may be fitted with an adapter to secure the tubing 25 into the inlet port 5. Suitable adapters include adapter 22, as shown in FIG. 12. The tubing 25 travels from the inlet port 5 through notch 14 located at the bottom edge of the bottom secure ring 13. The entire apparatus containing the magnetic stirbar 21 and tissue to be processed is placed on a magnetic stirrer and stirring is commenced. As the solvent flows through tubing 25 into the main vessel 1 and up through filter material 20, the solvent enters the small inner member. The small inner member contains the short inner vessel 12*b*, filter material 20, bottom secure ring 13 having one or more notches 14 provided on its bottom edge, top secure ring 11 and spacer 17. Spacer 17 may be as shown or may be provided with a top annular lip and/or a bottom annular lip. Any one or both of the top surface or the bottom surface of spacer 17 may be flat as shown, concave or convex. Stirring is begun as soon as sufficient fluid is present in the apparatus to permit suspension of the bone material being processed. Stirring and solvent flow are then adjusted to maintain the bone material in suspension and to achieve a linear change in the pH of the eluent acid with time and/or volume of acid pumped into the apparatus. The eluent exits the small inner member by flowing through the top filter material 20 located between the top secure ring 11 and the short inner vessel 12*b* and then through bore holes 18 of spacer 17 and finally out through eluent drain 9 provided in cover 8. The present process is carried out, for example when bone material is demineralized with an acidic solvent, for from about 2 minutes to about 12 minutes, more preferably from about 50 to about 250 minutes, and most preferably for about 80 minutes to 200 minutes. Eluent drain 9 may be provided with an adapter 23 which secures tubing 24. As illustrated, tubing 24 is press fitted over an end of the adapter 23. Again, a valve may be provided along the length of tubing 24 attached adapter 23. An in-line pH meter, or other means of monitoring a particular parameter, for example, calcium ion concentration, pH conductivity, or other, can be located at a point along the length of tubing 24 or 25. Once a particular desired parameter is reached, for example, if pH is being monitored and a 2% residual calcium level is desired, once the pH is in the range of 1.0±0.02, the solvent flow is stopped and any solvent within the apparatus is quickly drained through drain port 6.

Figure 13:
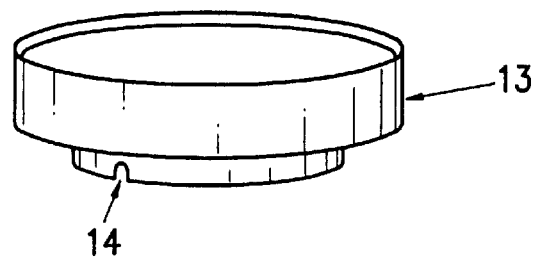
FIG. 13 illustrates a side view of bottom secure ring 13 having notch 14 provided at its bottom edge.

FIG. 13 illustrates a side view of bottom secure ring 13 having at its bottom edge notch 14.

Once the top secure ring and the bottom secure ring are pressed fitted into place, the bone tissue is held within the small inner vessel and contained by the filter material. The filter material allows the flow of solvents but prevents the passage of bone material. One of ordinary skill in the art can readily select an appropriate filter material based on the particular body tissue and the physical form of the tissue, for example, ground, minced, chips, strips, etc. In the case of bone, the filter material can readily be selected based on the size of the bone particles or pieces being processed. An additional factor that must be taken into account is the particular solvent or solvents being used. For example, bone in the size range of 250$\mu$ to 710$\mu$, bone cube and/or strips and/or chips, and being processed with an acidic solvent, would require the use of, for example, a polypropylene filter having a fine mesh in the range of from 50$\mu$ to 250$\mu$; more preferably from 125$\mu$ to 200$\mu$. Any material including any woven mesh which can withstand the solvent being used and which has the appropriate tensile strength, is contemplated for use in the present invention. The tensile strength must be sufficient to facilitate attachment of the mesh to the inner vessel via the secure rings. Mesh sizes in the above-recited ranges have the desirable tensile strength for use with the preferred embodiment of the present apparatus. One of ordinary skill in the are can readily determined appropriate mesh size and tensile strength without undo experimentation based on the tissue being processed, the solvents being used and the characteristics of the apparatus, for example, dimensions and material(s) it is composed of. Alternatively, the filter material may be integrally formed with the top and/or bottom secure ring and may be integrally formed out of the same or out of a different material, for example a plastic or a metal, for example stainless steel, titanium, etc. The integrally formed filter material may be configured as a screen, as a disk with holes, slits, etc. It is only critical that the integrally formed filter allow the flow of solvent but retain the tissue being processed.

Alternatively, the filter material may be formed as a separate member out of the same or different material as the apparatus, where the material is a disk which fits into the top and/or bottom secure ring where the secure ring is then fitted onto the inner vessel. Again, the disk may be configured as a screen, or with holes, slits, etc.

The approximate fluid capacity within the main body of the present controlled-flow apparatus using the large inner member is about 1.5 liters, whereas the fluid capacity within the main body when using the small inner member is about 1 liters.

The specific dimensions of the components of the present controlled-flow apparatus are not critical to the present invention. The exact dimension may be proportionally increased or proportionally decreased, as necessary, depending upon the type and volume of tissue being processed. In the case of particulate bone, the main body of the present preferred embodiment of the present controlled-flow apparatus contains cover 8 having a diameter of from about 25 to 35 cm, preferably about 27.5 cm, and a width of from 1 to 4 cm, preferably 2.4 cm. The main vessel 1 has a diameter of from about 15 to about 25 cm, preferably 19 cm; and a height of from about 8 to about 16 cm, preferably 12 cm. Likewise, in the case of bone tissue, the tall inner vessel 12a has a diameter of from about 12 to about 20 cm, preferably 16.5 cm; and a height of about 5 to 15 cm, preferably 10 cm. The short inner vessel 12b can have a similar diameter as the tall inner vessel, but the short inner vessel 12b has a height of less that of the tall inner vessel, for example from 3 to 13 cm, preferably 8 cm. Spacer 17 has a diameter equal to the diameter of the present short inner vessel, and a height of from about 2 to 7 cm, where the height of the spacer 17 and the height of the short inner vessel 12a is slightly less than the height of the main vessel 1 and approximates the height of the tall inner vessel 12b for example a total height of from 5 to 15 cm, preferably 10 cm.

Typically, solvents are introduced into the bottom of the container at a predetermined rate. As the container fills, stirring of the tissue is accomplished by a magnetic stirbar using a stirplate. Once the container is filled, fresh reagents are constantly introduced and removed by draining. Draining is accomplished by the passive draining of the column through the top, eluent drain 9. Once the prescribed pH level has been rended, the reagent is quickly removed by the drain port 6 located in the bottom of the vessel which may be controlled by a ball valve and or pump.

Again, once the apparatus is placed on top of a magnetic stirrer, a stirring bar 21 is added along with the tissue to be processed. Solvent, i.e. dilute (0.5 N) hydrochloric acid preferred in the case of bone, is pumped into the container from a preferably a generally deformable container. In-line filters may be used to ensure sterility of the solvent. The tissue, (i.e., bone particles) are maintained in suspension by vigorous stirring while the solvent (i.e., demineralization solution) is pumped into the container through the inlet port 5 and then through the bone at a rate sufficient to maintain a constant and approximately linear decline in pH of the eluent solution, for example, the flow rate is preferably 5 ml/min to 100 ml/min and out the top eluent drain 9. In-line pH probes may be used to monitor the pH of the eluent solution with the eluent acid being directed to waste. When the pH of the eluent solution has declined to a value appropriate to the desired level of residual calcium in the bone particles being demineralized, the demineralization process can be stopped by immediately draining the acid solution from the bone through the drain port 6, and washing the bone exhaustively with sterile water followed by a sodium phosphate buffer and/or potassium phosphate buffer at a concentration sufficient to achieve a pH between 5.5 and 7.4.

The resultant osteoinductive bone can then be removed from the controlled-flow apparatus and processed for storage, for example, the demineralized bone can then be freeze-dried. The osteoinductive potential of the ground demineralized bone can then be ascertained using the described in vitro and/or in vivo assays.

Any number of different solvents are contemplated for use with the present invention depending on the particular process in question. For example, one may wish to further treat osteoinductive bone subsequent to defatting and demineralization with antibacterial solutions, antifungal solutions, antiviral solutions, vitamins, bone morphogenetic protein or other osteogenic factors, collagens or other proteins. Also, prior to treatment with acid, tissue including bone may first be treated with a detergent or decontaminating solution to remove undesirable constituents, in the case of bone, to remove bone marrow elements prior to demineralization. These different solvents can be held in sterile form in any member of containers or reservoirs, for example, deformable containers.

The present controlled-flow apparatus may be formed from any material which is stable in the presence of the solvent being used and can include any one or more of the following: one or more plastics, stainless steel, titanium, one or more metals, etc. Any two or more components of the present apparatus may be separately formed or may be integrally formed as a single component. For example, tube-like inlet port 5 may be integrally formed with main vessel 1 or may be formed as a separate component.

III. Assays

A further embodiment of the present invention relates to the use of in vivo and/or in vitro assays to assess the osteoinductive potential of the produces osteoinductive ground bone. The in vivo assay involves the use of a commercially available athymic nude mouse (for example the nu/nu mouse, Charles River Laboratories) such as is known in the current art for use in assays of the osteoinductive potential of ground demineralized bone. The current invention includes the use of a specified amount (20 mg dry weight) of DBM (demineralized bone matrix) for a specified implant time interval (4 weeks) in muscles pouches in the gluteal region. Use of an athymic nude rat (also commercially available) permits implantation of more than two samples per animal, however the amount of materials implanted in each individual muscle pouch and the time of implantation remain the same. Implantation of amounts of DBM in excess of 20 mg results in lower osteoinduction (less new bone formation) due to micromotion of the implanted bone particles and a presumed excess of bone inductive/bone inhibitory factors.

The exact protocol for implantation of demineralized bone is as follows. The skin along a mid-dorsal line just above the hind legs is cut just through the fascia. The underlying muscles are exposed and bluntly dissected from the fascia. Materials to be implanted are inserted into the bluntly dissected muscle pouch. The muscle/fascia pouch is carefully sutured using polypropylene 4/0 and the skin is then carefully sutured again with 4/0 suture. A Michael wound chip is then used to pinch the skin together such that the mouse (or other mice) cannot chew the sutures off allowing the wound to open. After 4 weeks, the mouse is sacrificed using cervical dislocation and the implanted materials carefully dissected out (The material comes out as a "hard" piece of "gristle" and adherent soft tissue can be carefully dissected. The explant can be freeze-dried, weighted, solubilized in hydrochloric acid [normally use 1 N HCl overnight at 60° C.), and an aliquot used in the calcium assay. Calcium is expressed as a weight percent of the dry weight of the explant.

The current invention also relates to the use of the in vitro assay for assessing the osteoinductive potential of DBM. The current invention relates to the use of human periosteum-derived cell lines, for example the HPO/CB-MZ01 cell line described (available from LifeNet, Virginia Beach, Va.), in being induced to increase the levels of alkaline phosphatase enzyme produced in response to DBM and/or products and materials associated with the DBM. Presently, human periosteal cells are grown to confluence in alpha-minimum essential medium (MEM) supplemented with 10% (vol/vol) fetal calf serum. Following confluence of the cultured cells, the medium is changed to Dulbeccos minimum essential medium (DMEM) (MEM and DMEM are available from Sigma Chemical Company, St. Louis, Miss.) supplemented with 2% fetal calf serum and the DBM (5–10 mg) is added. After 5 days in culture, the cells are washed and harvested and assayed for levels of alkaline phosphatase using commercially available kits (for example, Sigma Chemical Company, St. Louis, Miss.).

The current invention relates to the levels of residual calcium to be present in demineralized bone. DBM demineralized to 1% to 4% residual calcium, preferably 1.5% to 3.5%, more preferably 1.8% to 2.5% residual calcium and most preferably 2.0% to 2.3%, is optimally and maximally osteoinductive. The apparatus and process described permits the controlled demineralization of ground bone to this maximally osteoinductive potential as determined by the level of residual calcium through monitoring of the pH of the eluent demineralization solution. Using the apparatus and process of the current invention, DBM demineralized to contain 2.0% to 2.3% residual calcium (as determined by the herein described in vivo and in vitro assays) is produced when the pH of the eluent solution is between pH 0.8 and pH 1.5, but optimally when the pH of the eluent solution is between pH 0.9 and pH 1.2.

Further details of the process of the invention are presented in the examples that follow:

EXAMPLE 1

Demineralization of Dental Bone

Properly sized ground bone (250µ to 710µ), 300 g wet weight, and stirbar were placed into the inner vessel of the present apparatus. The apparatus was closed and placed onto an external stirring drive. The apparatus was filled with 0.5 N hydrochloric acid with stirring begun as soon as sufficient fluid was present to permit suspension of the bone material. In this example, gas constituted an initial discharge through the outlet valve in that calcium carbonate, which constitutes a small percentage of the total calcium associated salts in the bone, was converted to carbon dioxide gas. As soon as the apparatus was full, stirring and acid flow were adjusted to maintain the bone material in suspension and to achieve a linear change in the pH of the eluent acid with time and/or volume of acid pumped into the apparatus. The initial pH of eluent approximated pH 3.0±0.5, however, the pH of the eluent acid slowly declined as the bone material was demineralized. The demineralization process was stopped, when the eluent solution pH was at 1.0±0.2, by quickly draining the demineralization apparatus and washing the bone with sterile distilled/deionized endotoxin-free water. After sufficient washing occurred to raise the pH of the bone materials to greater than about pH 3.0, the pH of the bone material was increased to approximately pH 6.5 to 7.4 by use of sodium/potassium phosphate buffer (0.001 to 0.1 M).

Aliquots of demineralized bone were removed for determination of residual calcium levels with the remainder of the bone material stored under refrigeration (or frozen) pending the outcome of the calcium assays. For analysis of calcium levels, 20 mg aliquots of freeze-dried bone were solubilized in 10 mls of hydrochloric acid. The acid was then neutralized by adding sodium hydroxide. Aliquots (100 microliter) of the solubilized bone was added to 4 mls of Arsenazo III reagent (0.05% in Tris buffer) and vortexed. Absorbance were read at 650 nm and the concentration of calcium was determined from a standard curve generated using $CaCo_3$. The total about of calcium in the acid solubilization solution was calculated and divided by the amount of bone solubilized to calculate the mg calcium/mg dry weight of bone. The calcium content of the bone is expressed as a wt % calcium of the dry weight of bone. If the desired wt % residual calcium has been achieved, the remainder of the bone material may be processed using standard procedures such as for example, freeze-drying and packaging. If the wt % residual calcium is greater than that desired, the bone may be returned to the controlled-flow apparatus and further demineralized. If the wt % residual calcium is less than that desired, the remainder of the bone material can be resuspended in calcium phosphate, for example 2.0 to 0.05 M $CaHPO_4$, at pH 2.0 to 3.0 depending on the concentration of calcium phosphate needed to restore the overly demineralized bone to a state of being maximally osteoinductive. The pH of the calcium phosphate solution is increased to pH 6.0 to 8.0 after an incubation period demonstrated to allow the calcium phosphate to diffuse evenly throughout the demineralized bone. In the present case, for example for bone particles in the 250µ to 710µ particle size range, this incubation interval will approximate 5 to 10 minutes. The bone is then exhaustively washed with water to remove residuals of calcium phosphate precipitate not present within or absorbed onto the bone particles.

Figure 23:
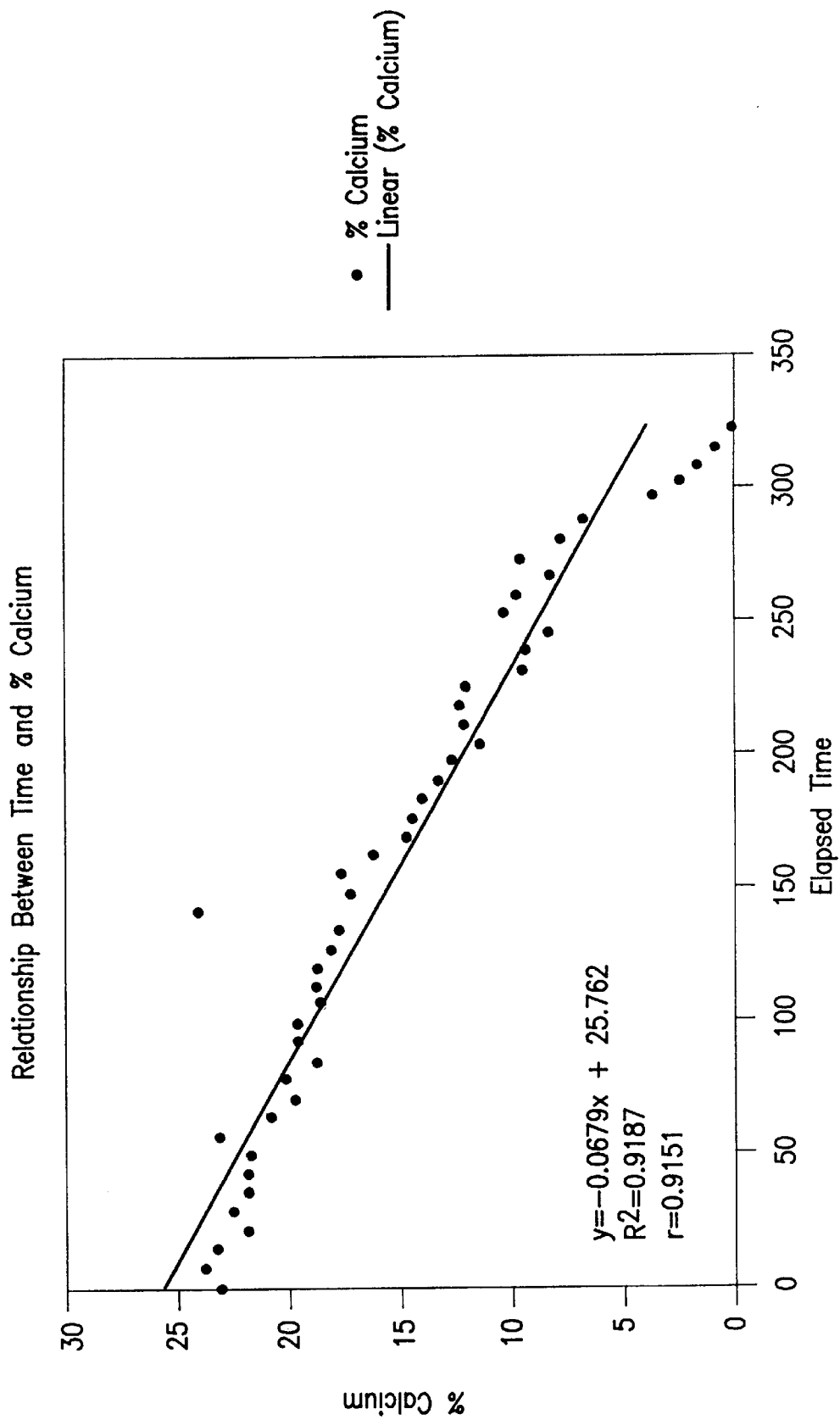
FIG. 23 illustrates a linear relationship between wt % residual calcium in demineralized bone and the time of exposure to the demineralization process, Run No. 1.
Figure 24:
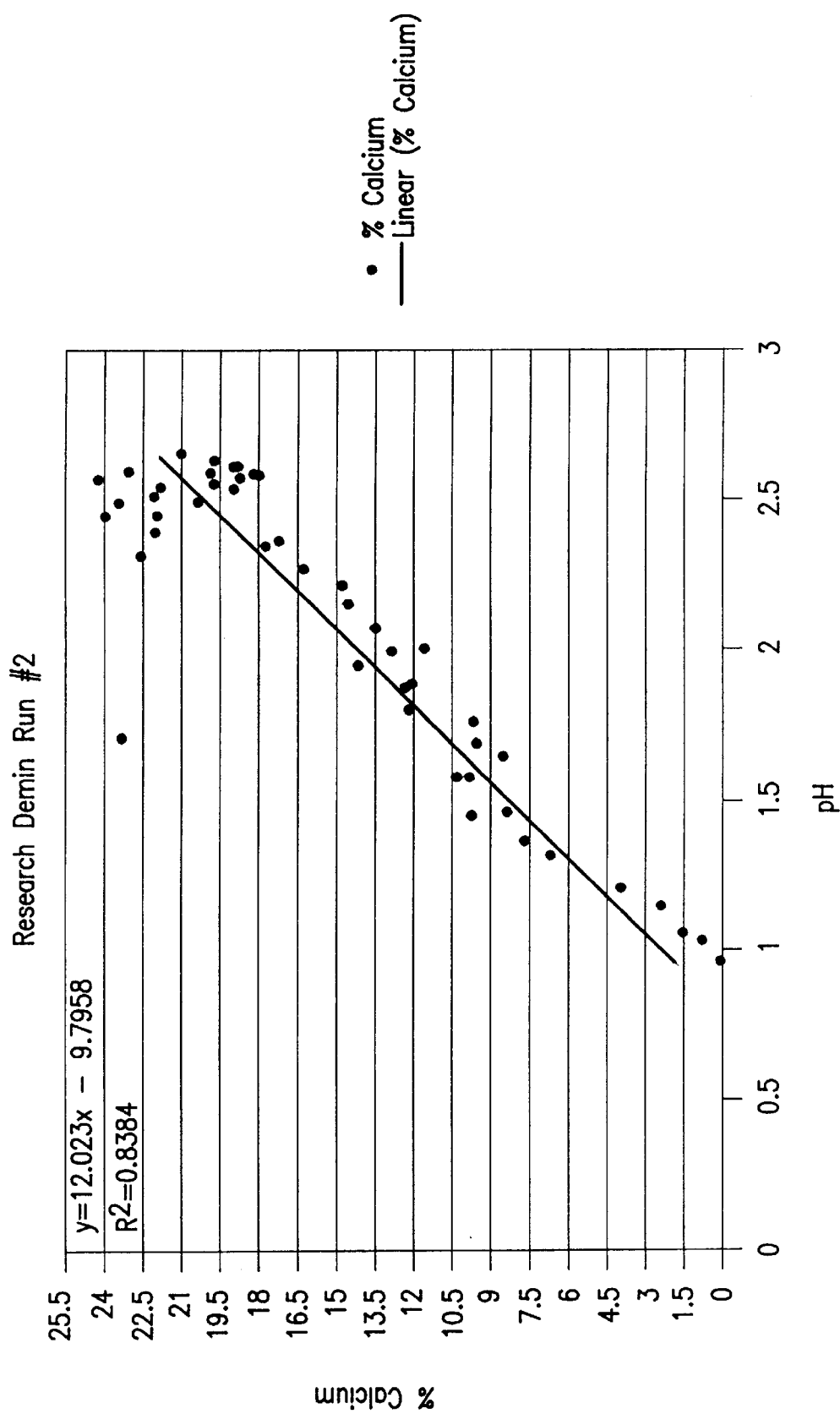
FIG. 24 illustrates an analysis of pH eluent solution during a demineralization of ground bone plotted as a function of the wt % residual calcium in bone sampled at the time the pH value of the eluent solution was collected for Run No. 1.
Figure 25:
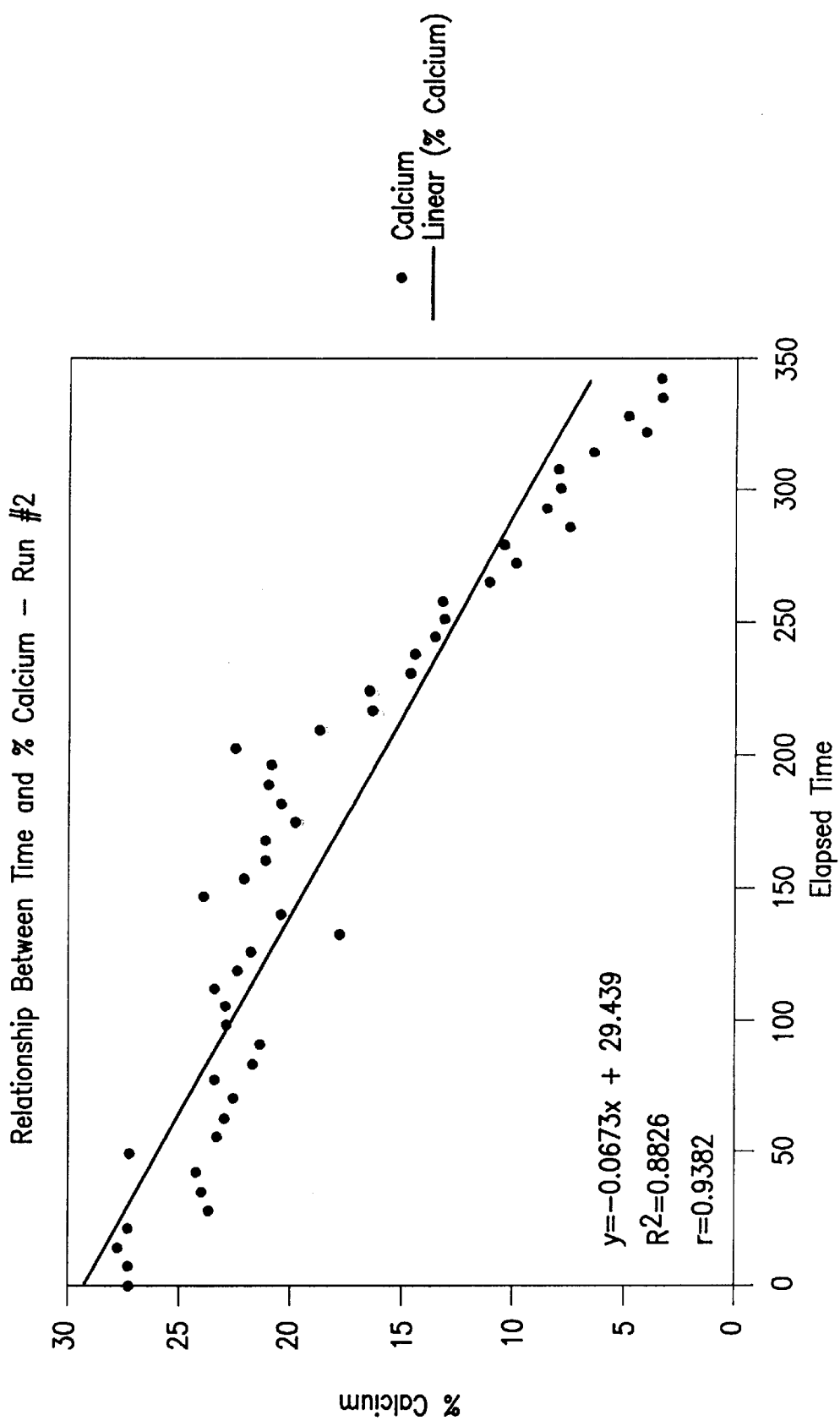
FIG. 25 illustrates a linear relationship between wt % residual calcium in demineralized bone and the time of exposure to the demineralization process, Run No. 2.
Figure 26:
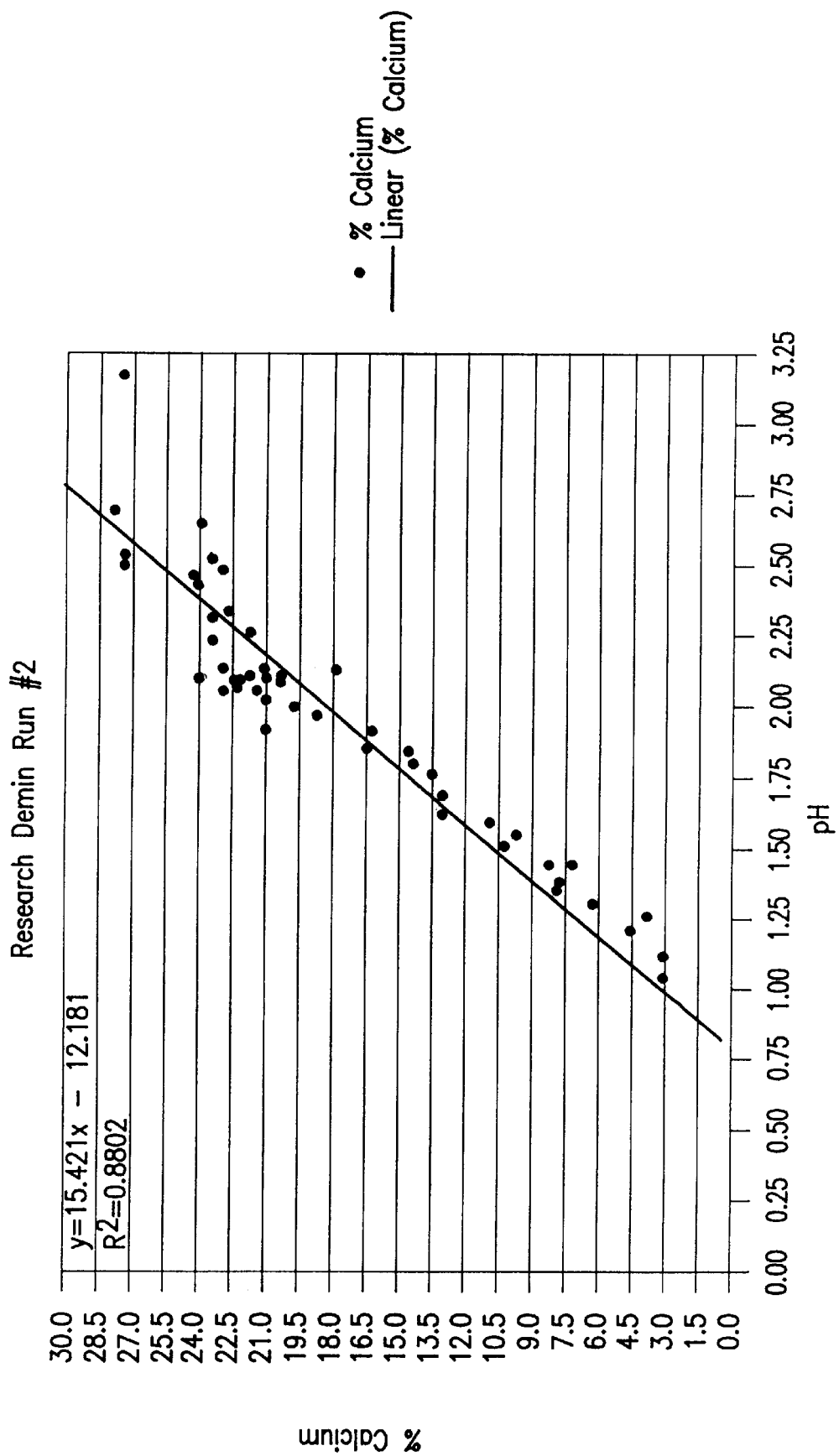
FIG. 26 illustrates an analysis of pH eluent solution during a demineralization of ground bone plotted as a function of the wt % residual calcium in bone sampled at the time the pH value of the eluent solution was collected for Run No. 2.
Figure 27:
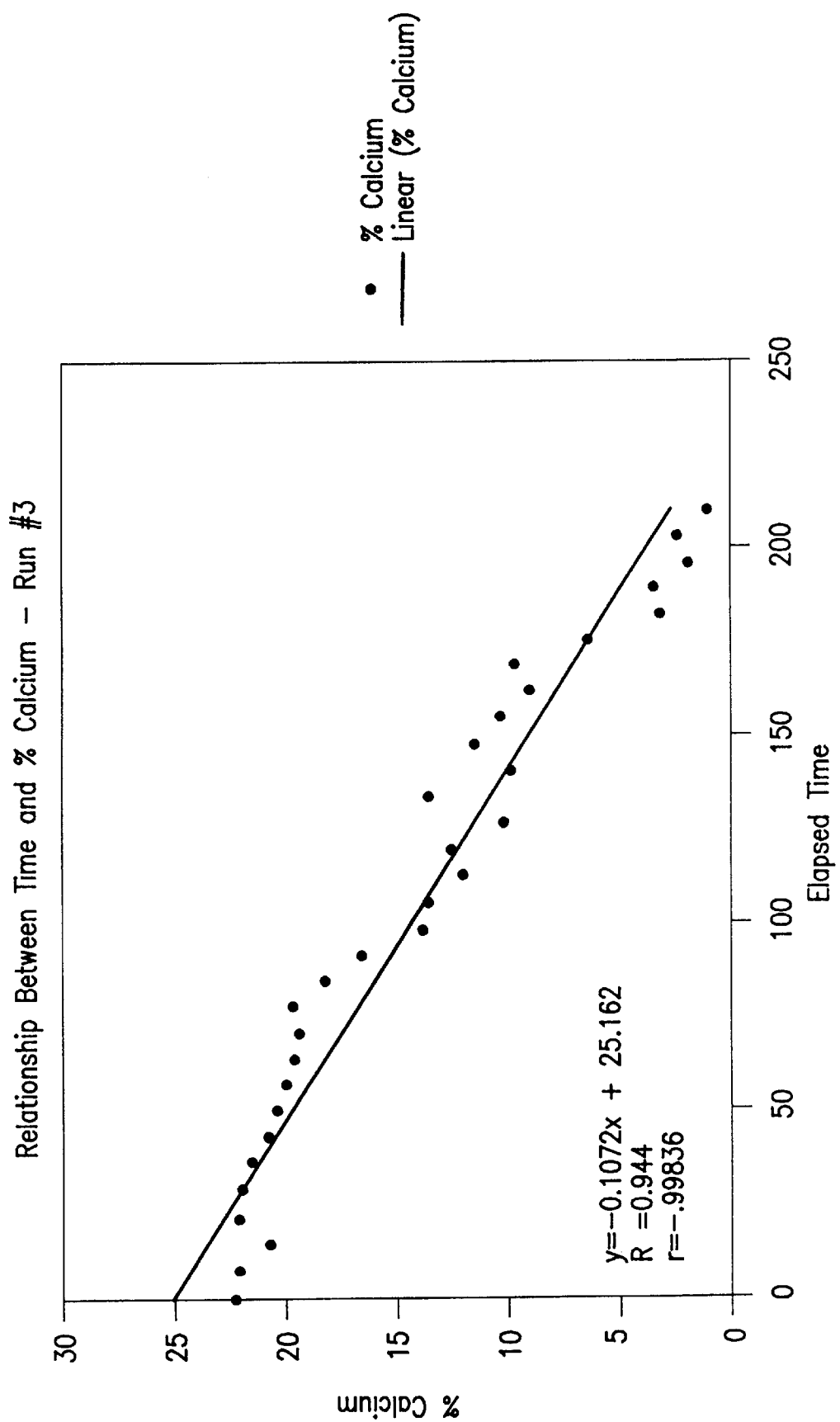
FIG. 27 illustrates a linear relationship between wt % residual calcium in demineralized bone and the time of exposure to the demineralization process, Run No. 3.
Figure 28:
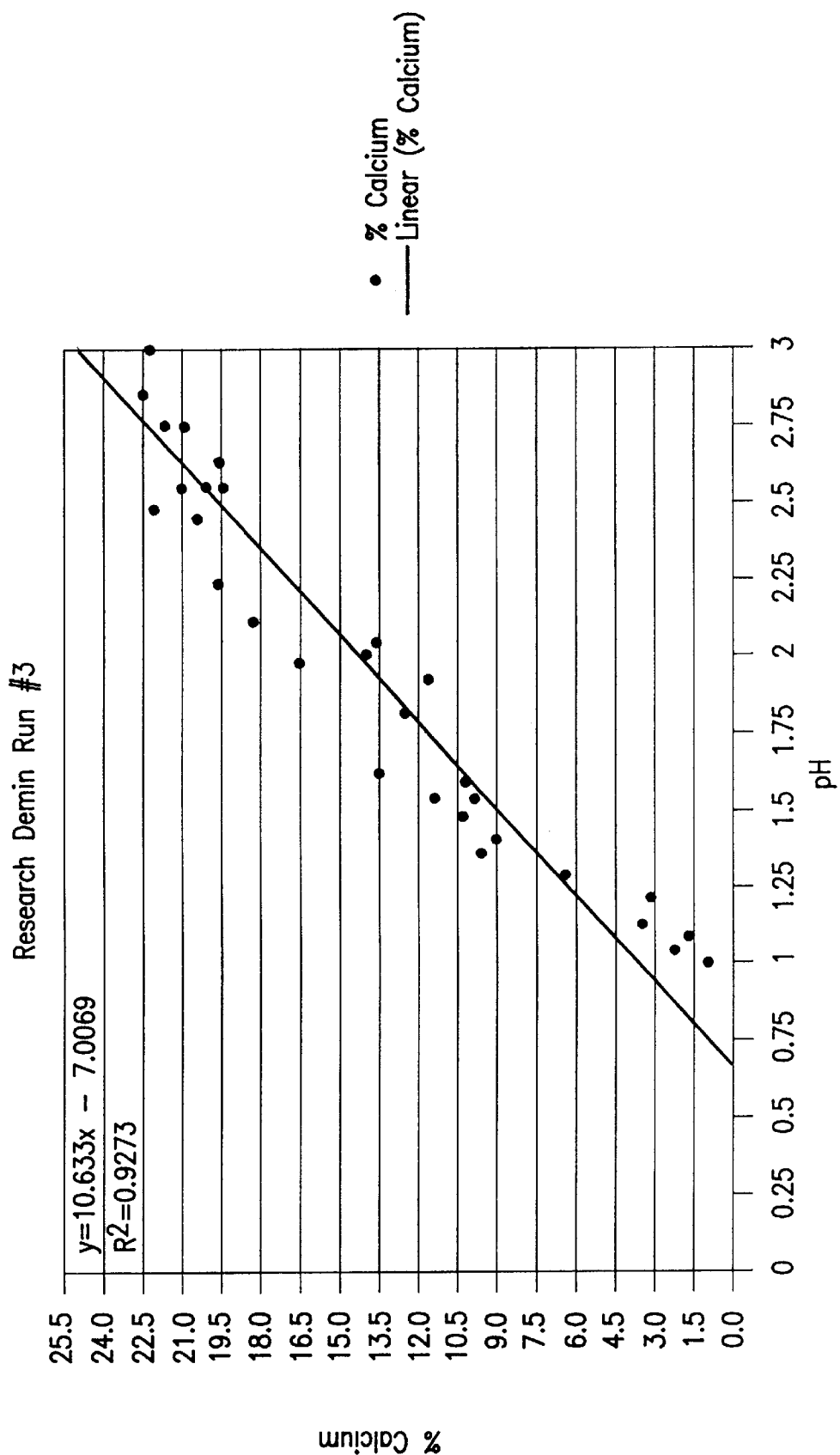
FIG. 28 illustrates an analysis of pH eluent solution during a demineralization of ground bone plotted as a function of the wt % residual calcium in bone sampled at the time the pH value of the eluent solution was collected for Run No. 3.

As illustrated in FIGS. 23, 25, and 27 (three separate demineralization procedures), the percent residual calcium in bone being demineralized in this example decreases in an appropriate linear fashion over an approximate 300 minutes of demineralization. As the bone is demineralized, less and less calcium phosphate (a strong buffer and the primary mineral component of bone) is solubilized from the bone particles and as buffering capacity of salts in the eluent decreases, pH of the eluent decreases. It is thus possible, using this current methodology, to correlate eluent pH with percent residual calcium in the bone powder being demineralized. FIGS. 24, 26, and 28 (three separate demineralization procedures) clearly demonstrate the linear relationship obtained between percent residual calcium in bone being demineralized under this methodology and eluent pH. Thus, using eluent pH (as one parameter) it is possible to accurately predict when bone has been optimally demineralized.

Demineralized bone determined to contain the desired wt % residual calcium is then processed according to standard protocols for clinical distribution.

EXAMPLE 2

Demineralization of Dental Bone

Properly sized ground bone (250µ to 710µ), 300 grams wet weight, and a stirbar were placed into the inner vessel of the controlled-flow apparatus. The apparatus was closed and placed onto an external stirring drive. The apparatus was filled with 0.5 N hydrochloric acid with stirring begun as soon as sufficient fluid was present to permit suspension of the bone material. As soon as the apparatus was full, stirring and acid flow were adjusted to maintain the bone material in suspension and to achieve a linear change in the pH of the eluent acid with time and/or volume of acid pumped into the apparatus. The initial pH of the eluent approximated pH 3.0±0.5, however, the pH of the eluent acid slowly declined as the bone material was demineralized. The demineralization process was stopped, when the eluent solution pH was at 1.0±0.2, by quickly draining the apparatus through the drain port 6 and washing the bone with sterile distilled/deionized endotoxin-free water. After sufficient washing occurred to raise the pH of the bone materials to greater than about pH 3.0, the pH of the bone material was increased to approximately pH 6.5 to 7.4 by use of sodium/potassium phosphate buffer (0.001 to 0.1 M). As illustrated in FIGS. 23, 25, and 27 (three separate demineralization procedures), the percent residual calcium in bone being demineralized in this example decreases in an approximate linear fashion over an approximate 300 minutes of demineralization. As the bone was demineralized, less and less calcium phosphate (a strong buffer and the primary mineral component of bone) was solubilized from the bone particles and as buffering capacity of salts in the eluent decreases, pH of the eluent decreases. It is thus possible, using this current methodology, to correlate eluent pH with percent residual calcium in the bone powder being demineralized. FIGS. 24, 26, and 28 (three separate demineralization procedures) clearly demonstrate the linear relationship obtained between percent residual calcium in bone being demineralized under this methodology and eluent pH. Thus, using eluent pH (as one parameter) it is possible to accurately predict when bone has been optimally demineralized.

Aliquots of demineralized bone were then removed for determination of residual calcium levels with the remainder of the bone material stored under refrigeration (or frozen) pending the outcome of the calcium assays.

For analysis of calcium levels, 20 mg aliquots of freeze-dried bone were solubilized in 10 mls of 1 N hydrochloric acid. Aliquots (50 microliter) of the solubilized bone were added to 4 mls of DMA® reagent (Sigma Chemical Company, St. Louis, Mo.) and vortexed. Absorbance was read at 570 nm within 15 minutes and the concentration of calcium was determined from a standard curve generated using $CaCO_3$. Calcium reacts with Cresolpthalein complexone to form a colored complex that is measured spectrophotometrically at 570 nm. The total amount of calcium in the acid solubilization solution was calculated and divided by the amount of bone solubilized to calculate the mg calcium/mg dry weight of bone. The calcium content of the bone is expressed as a wt % calcium of the dry weight of bone. If the desired wt % residual calcium has been achieved, the remainder of the bone material is processed using standard procedures such as for example, freeze-drying and packaging. If the wt % residual calcium is greater than that desired, the bone is returned to the controlled-flow apparatus and further demineralized. If the wt % residual calcium is less than that desired, the remainder of the bone material is resuspended in calcium phosphate, for example 2.0 to 0.05 M $CaHPO_4$, at pH 2.0 to 3.0 depending on the concentration of calcium phosphate needed to restore the overly demineralized bone to a state of being maximally osteoinductive. The pH of the calcium phosphate solution is increased to pH 6.0 to 8.0 after an incubation period demonstrated to allow the calcium phosphate to diffuse evenly throughout the demineralized bone. In the present case, for example for bone particles in the $250\mu$ to $710\mu$ particle size range, this incubation interval will approximate 5 to 10 minutes. The bone is then be exhaustively washed with water to remove residuals of calcium phosphate precipitate not present within or absorbed onto the bone particles.

Following the demineralization process, the bone materials may be further subjected to treatment with 70% (vol:vol) isopropyl alcohol by pumping the alcohol into the controlled-flow apparatus, initiating stirring and suspension of the bone particles in the alcohol solution as soon as sufficient alcohol is available to permit suspension of the bone particles. The alcohol is pumped through the bone materials until lipids in the eluent solution are below a desired limit or until lipids no longer precipitate out when eluent solution is dropped into deionized water. The alcohol solution is displaced from the bone materials in the controlled-flow apparatus using the peristaltic pump and alcohol solution is replaced with a continuous flow of secondary treatment solution. The agents present in this secondary treatment solution may include antibacterial, antifungal, and/or antiviral agents, hydrogen peroxide, surfactants, growth factors, vitamins, minerals, or any number of agents demonstrated to enhance graft acceptance and/or function following implantation.

Figure 14:
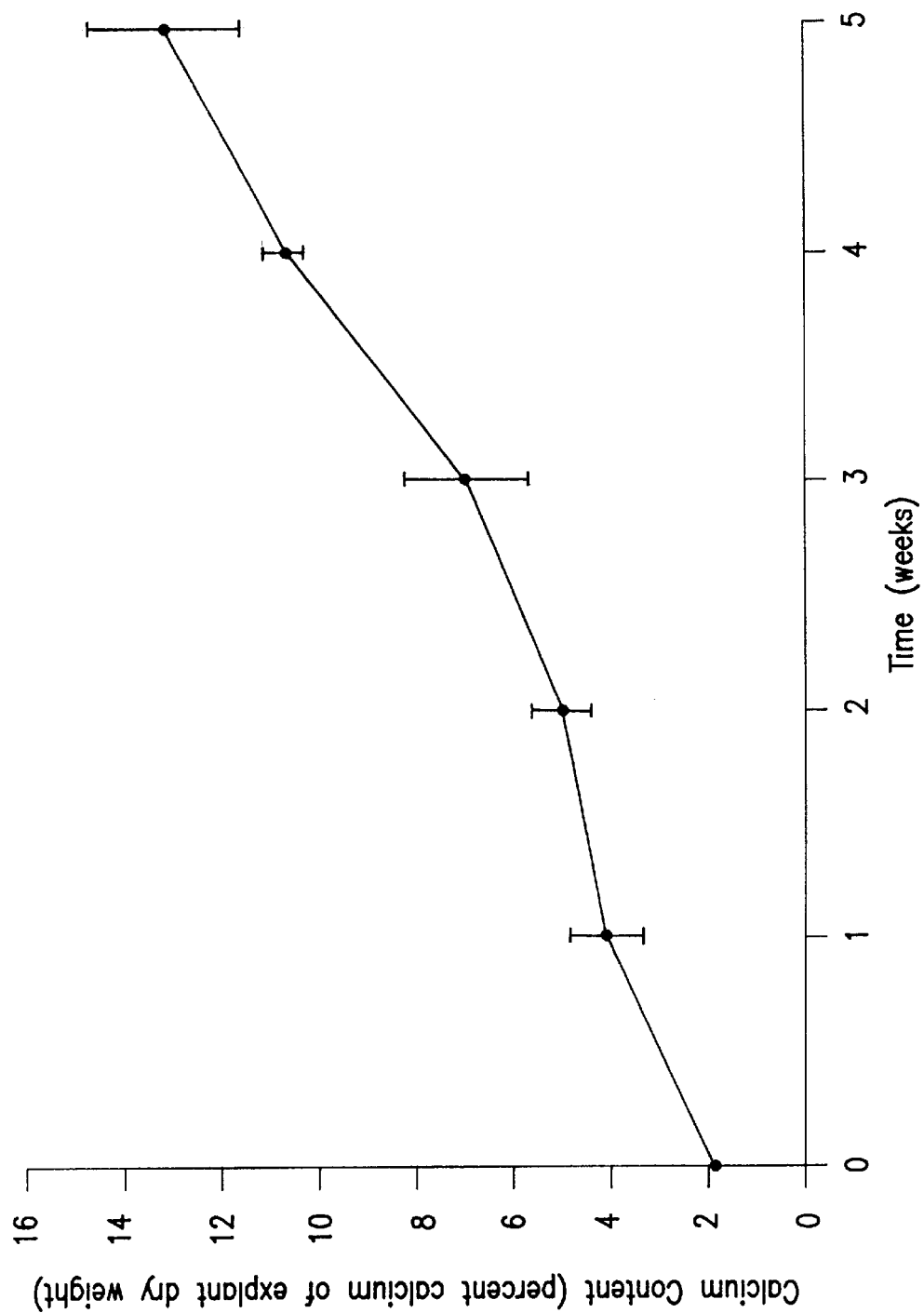
FIG. 14 illustrates the time course of implant remineralization.
Figure 15:
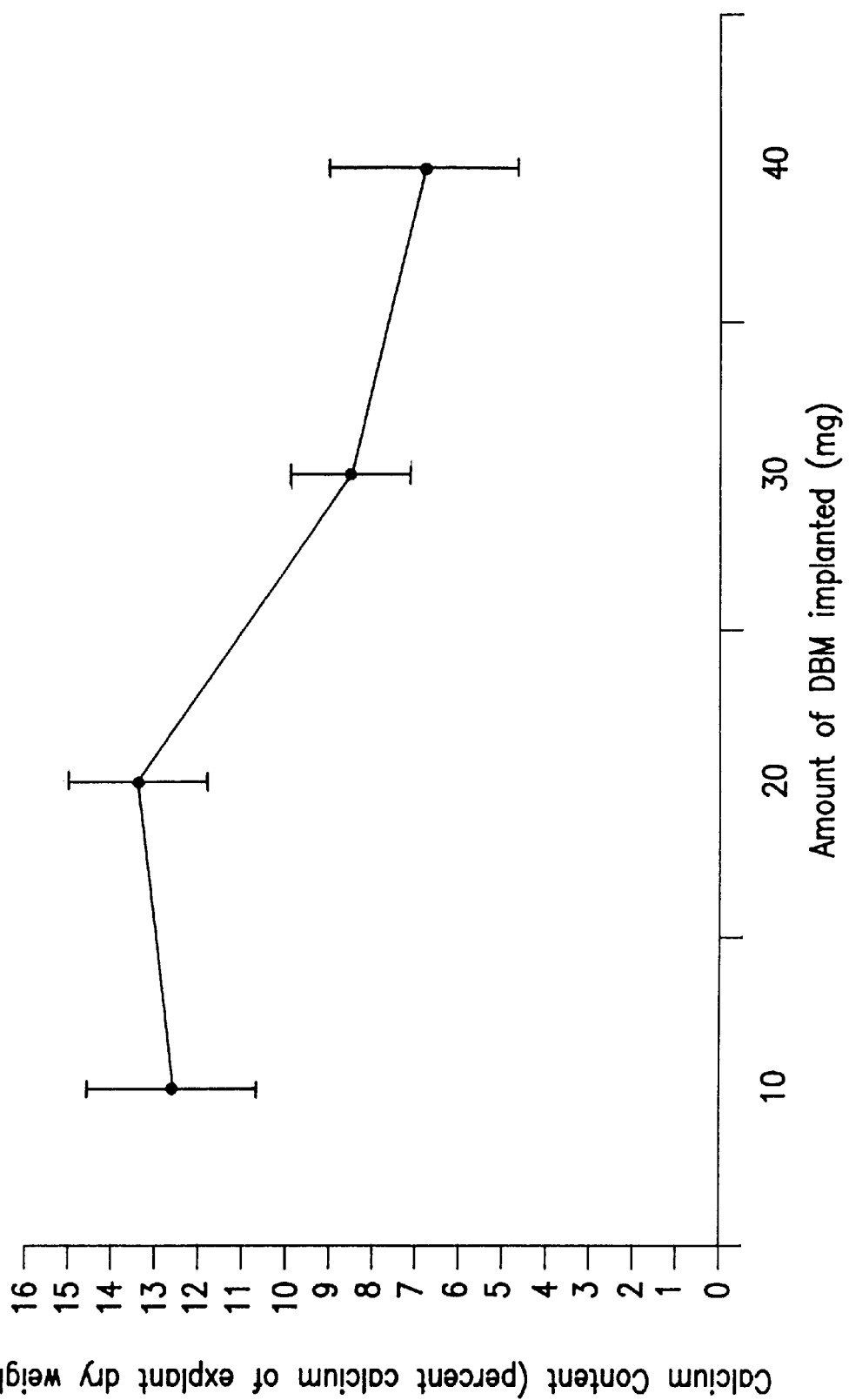
FIG. 15 illustrates the in vivo (nude mouse assay) dose response data.
Figure 16:
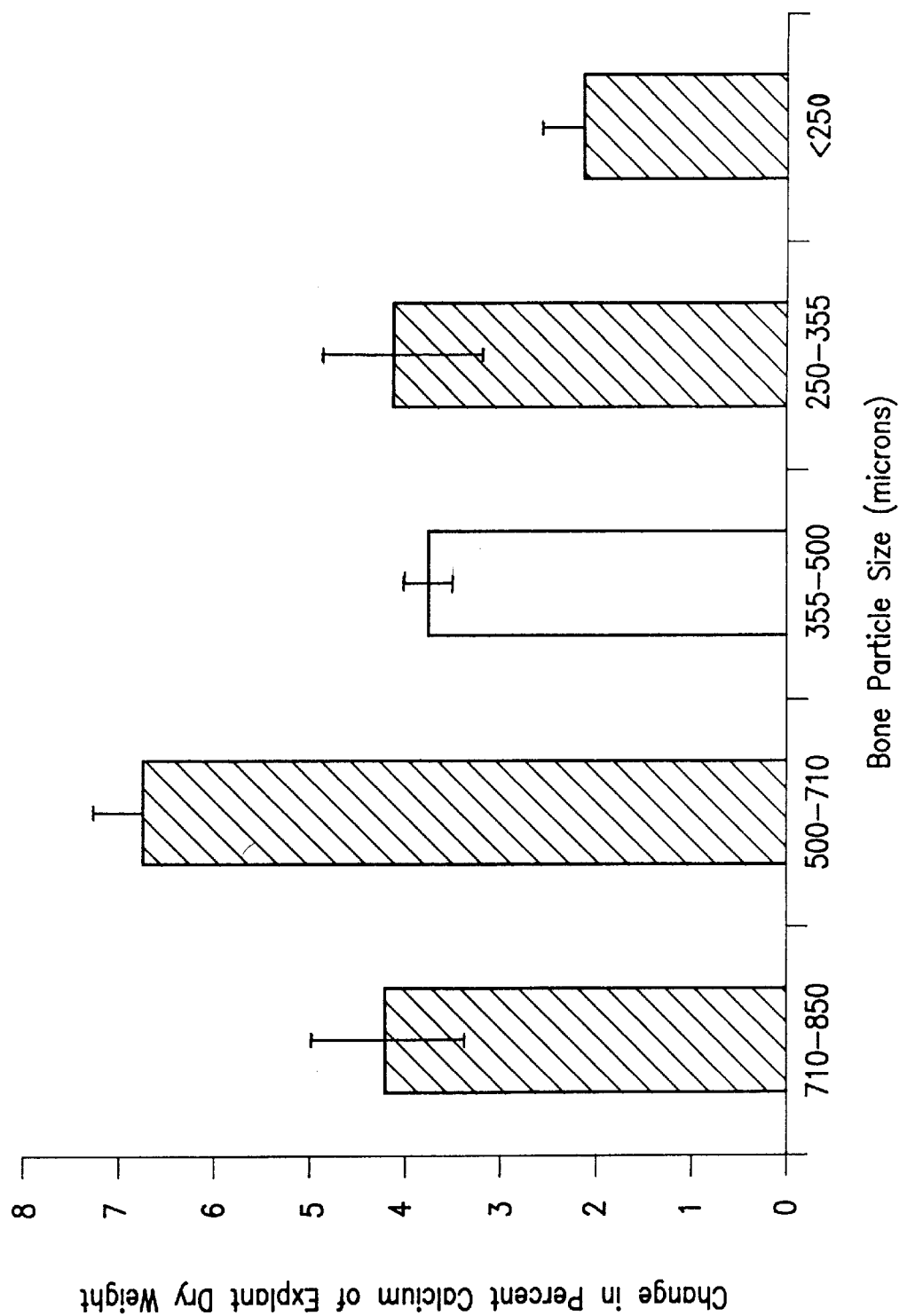
FIG. 16 illustrates the explant weight of implanted (20 mg) DBM after 4 weeks in the nude mouse, in vivo, assay system versus bone particle size.
Figure 20:
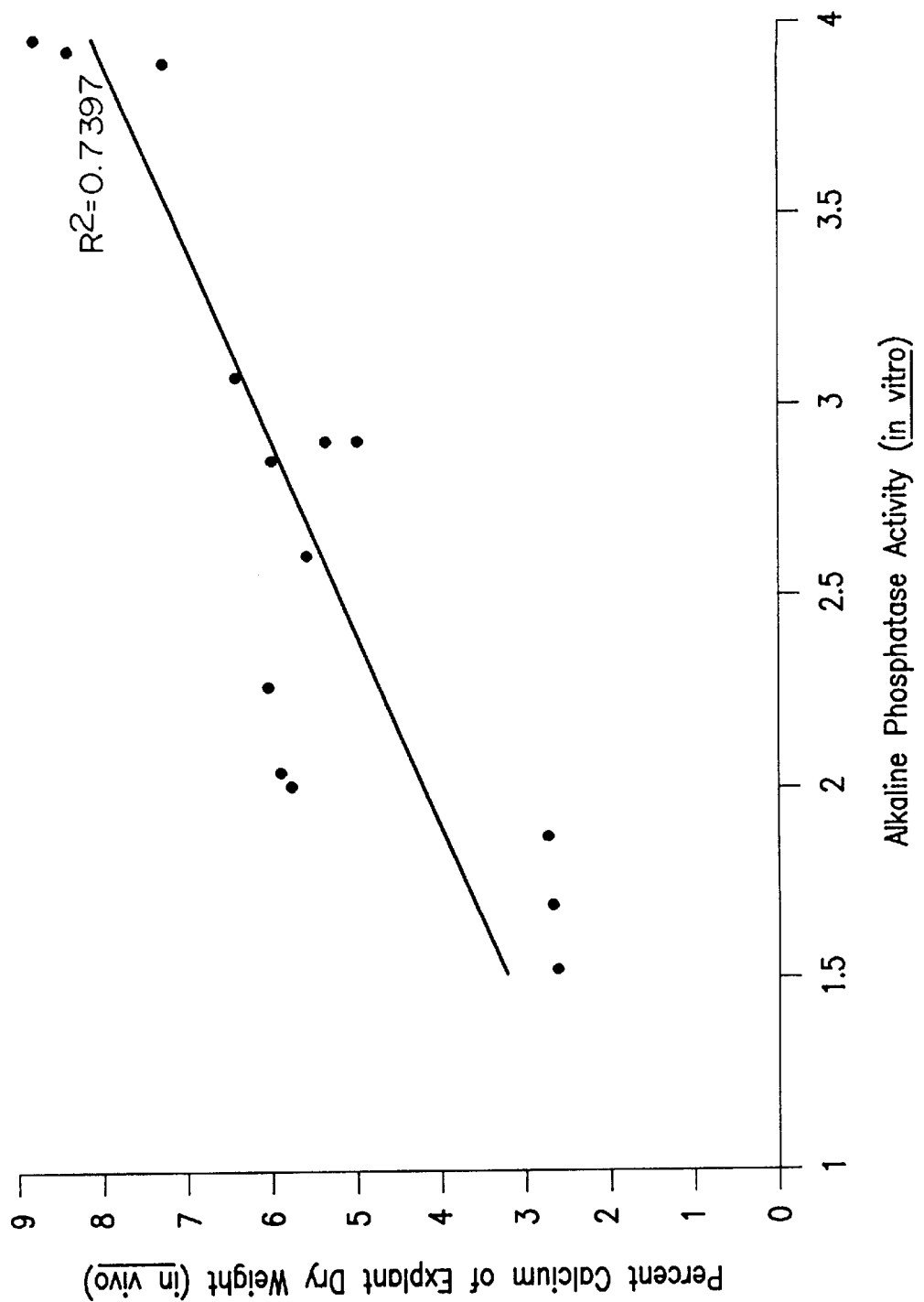
FIG. 20 illustrates the correlation of the in vivo and in vitro assays of demineralized bone obtained from different donors.
Figure 21:
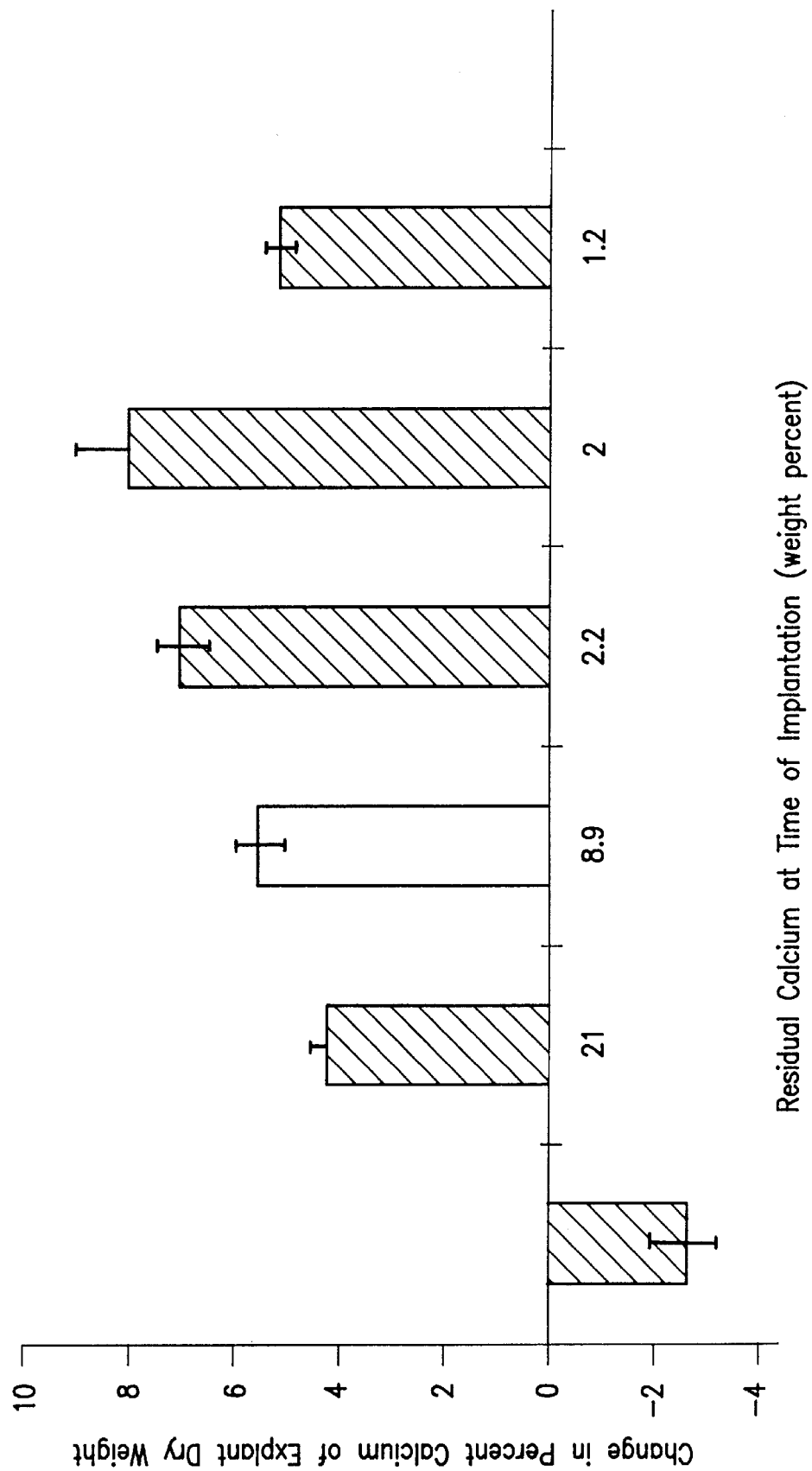
FIG. 21 illustrates the effect that wt % residual calcium in demineralized bone has on subsequent remineralization potential following implantation into the athymic nude mouse muscle pouch for 4 weeks, i.e. the in vivo assay.

Demineralized bone determined to contain the desired wt % residual calcium, lipid content, and/or additional supplement is then processed according to standard protocols, such as for example, freeze-drying and packaging, etc., for clinical distribution. Aliquots of the demineralized bone powder prepared and ready for clinical distribution may be assessed for their potential for inducing new bone formation in a clinical application by assaying the bone powder in the in vivo assay described herein. For this analysis, adult male athymic mice (nu/nu) were injected intraperitoneal with 0.1 cc Aceopromazine and 0.1 cc sodium phenobarbitol. The mice were fully anesthetized in about 5 minutes at which time the back of each mouse was disinfected using 70% isopropyl alcohol. A 1 to 2 cm incision was made along the dorsal midline, through the skin and subcutaneous tissue near the gluteal region. The fascia of the longissimus dorsi muscle was bluntly dissected, a small incision was made in the fascia, and a muscle pouch was created by bluntly dissecting the fascia from the muscle. Samples DMB (10 or 20 mg, FIG. 15) to be implanted were placed into the muscle pouch (bilaterally) and the muscle pouch loosely closed with sutures of 6/0 polypropylene (the muscle pouch provides the best site for the implantation of DMB where remineralization is being assessed). As illustrated in FIG. 16 maximally osteoinductive potential is exhibited by DMB in the 500 to $710\mu$ particle size range. Particles smaller than about $250\mu$ are significantly less osteoinductive and are resorbed when implanted in muscle pouch of athymic mice (data not shown). The skin and subcutaneous tissue was also closed with two or three sutures of 6/0 polypropelene and 9 mm Michael wound clips are placed over the sutures skin to prevent reopening of the implantation sites. The mice were kept warm until they revived, at which time they were returned to a pathogen-free/autoclaved mouse box with filter and returned to the vivarium. After 4 weeks, the mice were sacrificed by cervical dislocation and the implants carefully dissected. Excess soft tissue was removed from the surface of the hard-gristly implant (now referred to as an explant) and the explant was freeze-dried. The freeze-dried explant was solubilized in hydrochloric acid and analyzed for percent residual calcium. As shown in FIG. 14, the percent calcium in explanted DMB increases as an approximate linear function of implant time for properly demineralized DMB, i.e., demineralized to approximately 2 wt % residual calcium (FIG. 21), implanted in muscle pouches of athymic mice. As illustrated in FIG. 20, the in vivo and in vivo assays correlated in their predictive potential approximately 74% of the time.

EXAMPLE 3

Demineralization of Dental Bone

Properly sized ground bone (250µ to 710µ), 300 grams wet weight, and stir bar were placed into the inner vessel of the controlled-flow apparatus. The apparatus was closed and placed onto an external stirring drive. The apparatus was filled with Allowash™ Solution with stirring begun as soon as sufficient fluid was present to permit suspension of the bone material. Approximately 1 to 4 liters of this detergent solution was pumped through the bone materials to achieve a cleaning and lipid extraction processing. The detergent solution was then removed from the demineralization apparatus by connecting a container of 0.5 N hydrochloric acid to tubing 25 attached to inlet port 5, and initiating the demineralization process. Stirring and acid flow rates were adjusted to maintain the bone material in suspension and to achieve a linear change in the pH of the eluent acid with time and/or volume and acid pumped into the apparatus. The initial pH of eluent approximated pH 3.0±0.5, however, the pH of the eluent acid slowly declined as the bone material was demineralized. The demineralization process was stopped, when the eluent solution pH reached 1.0±0.2, by quickly draining the controlled-flow apparatus through drain port 6 and washing the bone with sterile distilled/deionized endotoxin-free water. After sufficient washing occurred to raise the pH of the bone materials to greater than about pH 3.0, the pH of the bone material was increased to approximately pH 6.5 to 7.4 by use of sodium/potassium phosphate buffer (0.001 to 0.1 M).

Aliquots of demineralized bone were then removed for determination of residual calcium levels with the remainder of the bone material stored under refrigeration (or frozen) pending the outcome of the calcium assays. If the desired wt % residual calcium has been achieved, the remainder of the bone material may be processed using standard procedures such as for example, freeze-drying and packaging. If the wt % residual calcium is greater than that desired, the bone may be returned to the inner vessel and further demineralized. If the weight percent residual calcium is less than that desired, the remainder of the bone material can be resuspended in calcium phosphate, for example 2.0 to 0.05 M $CaHPO_4$, at pH 2.0 to 3.0 depending on the concentration of calcium phosphate needed to restore the overly demineralized bone to a state of being maximally osteoinductive. The pH of the calcium phosphate solution is increased to pH 6.0 to 8.0 after an incubation period demonstrated to allow the calcium phosphate to diffuse evenly throughout the demineralized bone. In the present case, for example for bone particles in the 250µ to 710µ particle size range, this incubation interval will approximate 5 to 10 minutes. The bone may then be exhaustively washed with water to remove residuals of calcium phosphate precipitate not present within or absorbed onto the bone particles.

Figure 17:
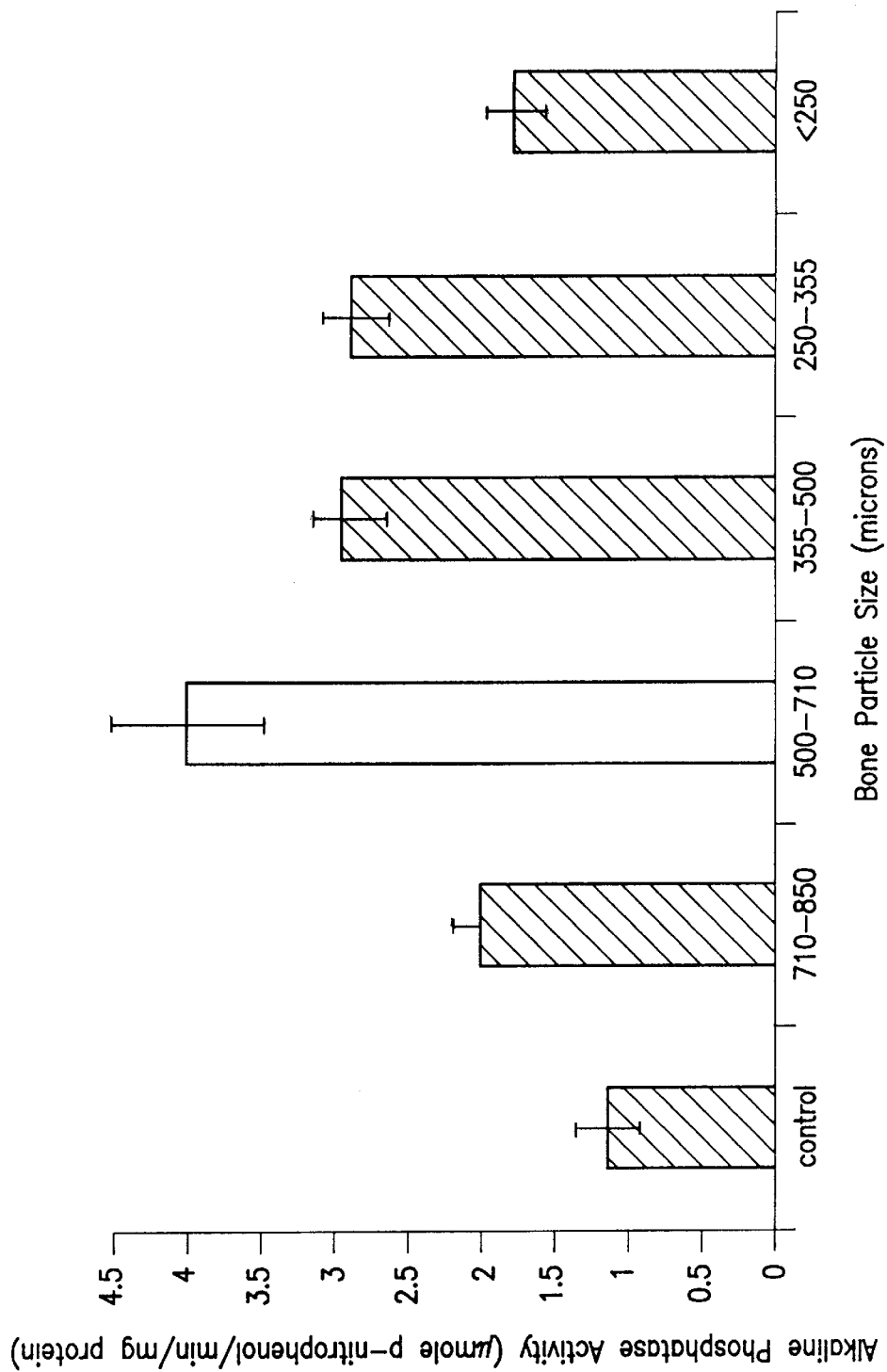
FIG. 17 illustrates the alkaline phosphatase levels in HPO/CB-MZ01 cells incubated for five days in the presence and absence (control) of demineralized bone particles in the size ranges specified.
Figure 18:
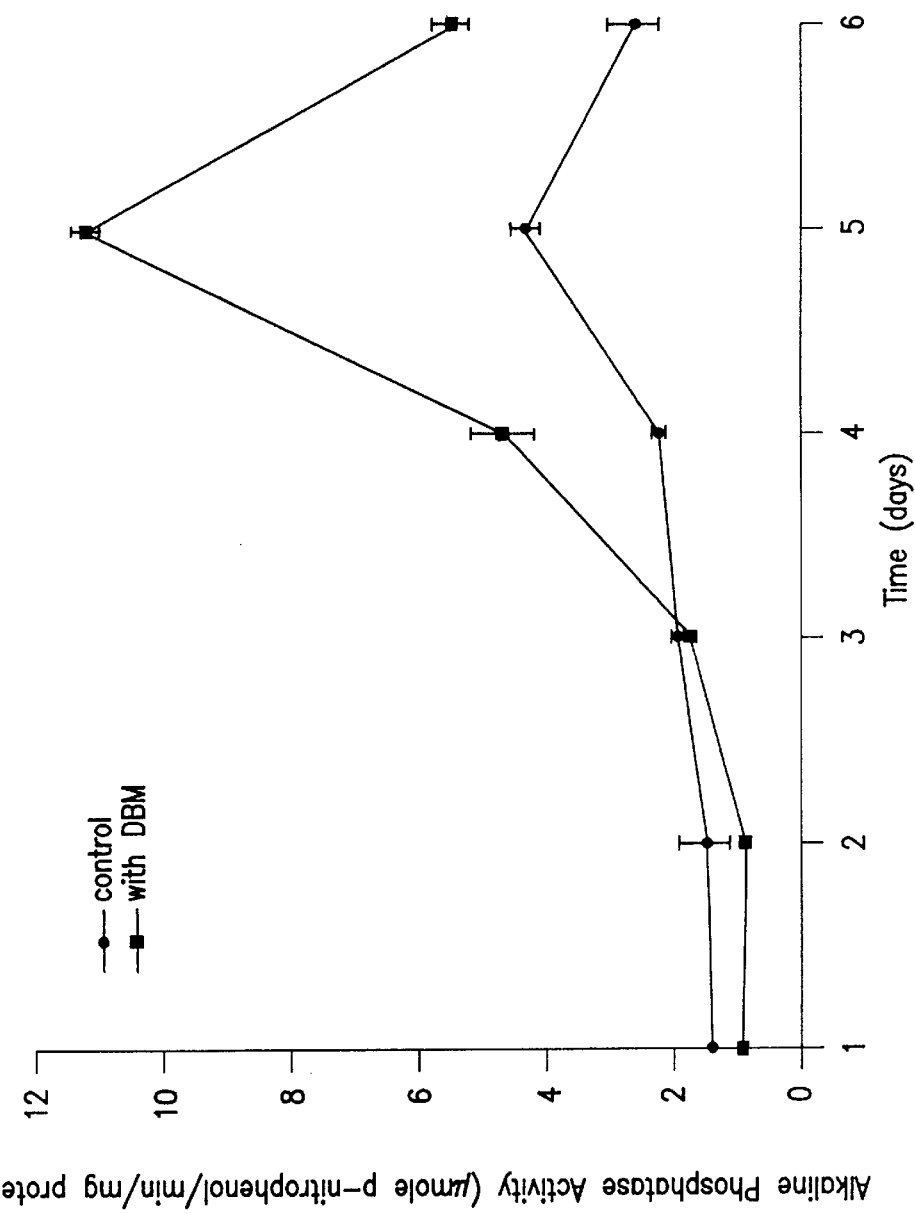
FIG. 18 illustrates the time course of alkaline phosphatase induction in the HPO/CB-MZ01 cell line in the presence and absence of ground demineralized human bone (particle size range 250–710μ).
Figure 19:
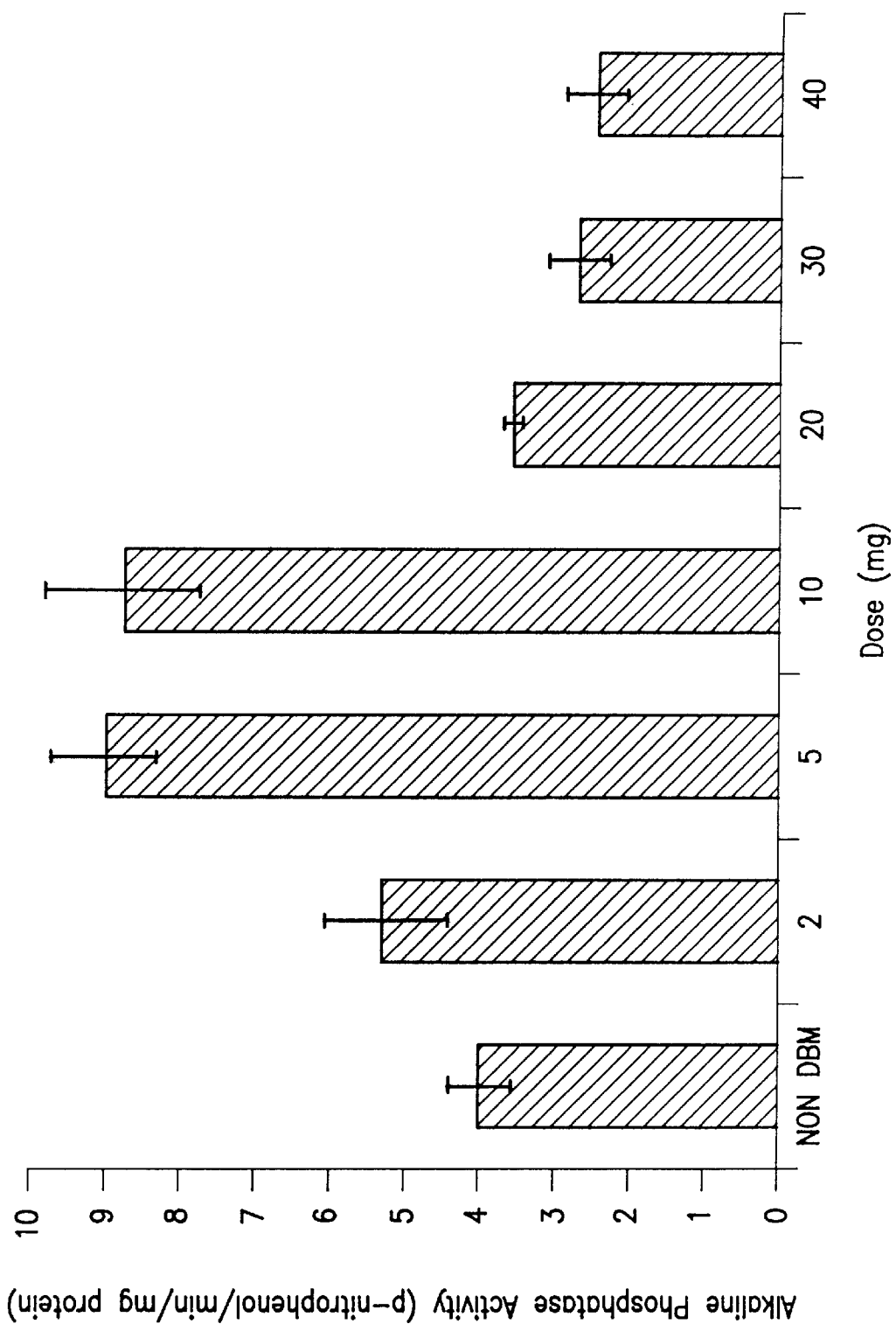
FIG. 19 illustrates the dose response curve describing the increase in alkaline phosphatase activity in the human periosteal cells as a function of the amount of demineralized bone added to the cultured cells.
Figure 22:
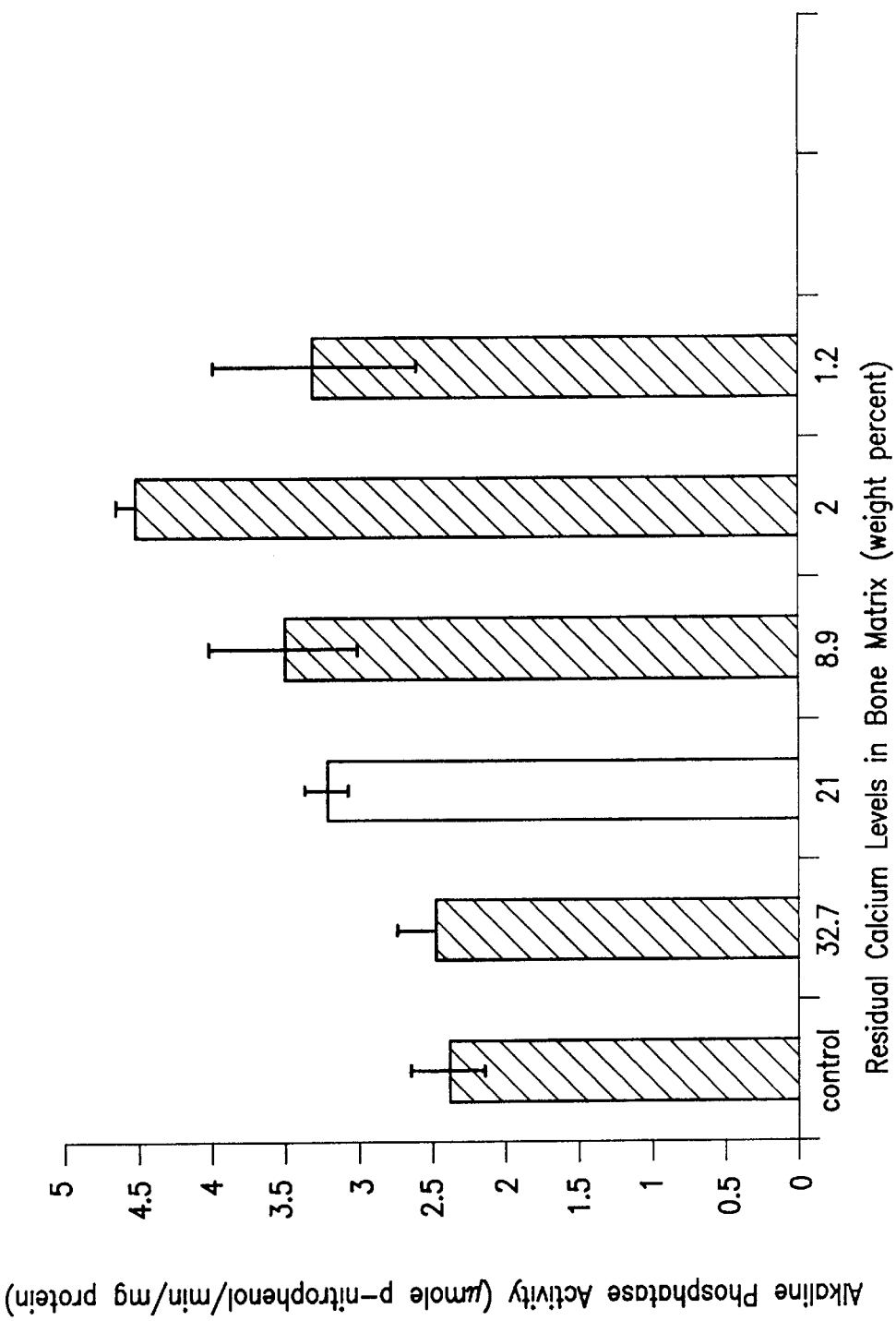
FIG. 22 illustrates the effect that wt % residual calcium in demineralized bone has on subsequent induction of alkaline phosphatase (at 5 days of incubation) following addition to confluent cultures of human periosteal cells.

Demineralized bone determined to be optimally demineralized (i.e., determined to contain the desired wt % residual calcium) was then processed according to standard protocols for clinical distribution. Aliquots of the demineralized bone powder prepared and ready for clinical distribution were assessed for their potential for inducing new bone formation in a clinical application by assaying the bone powder in the in vitro assay described herein. For this analysis, periosteal cells (for example the HPO/CB-MZ01 cell line established by LifeNet) derived from human periosteum were thawed from their cryopreserved state (from a Cell Bank) and cultures initiated in tissue culture flasks. The cells were grown to confluency in alpha-Minimum Essential Medium (αMEM) supplemented with 10% (vol/vol) fetal calf serum (FCS) (Sigma Chemical Company, St. Louis, Mo.) in a $CO_2$ incubator at 5% $CO_2$ and 37° C. Just prior to confluency, the cells were "split" by releasing the attached cells with trypsin/EDTA reagent (Sigma Chemical Company, St. Louis, Mo.) and dividing the cells from one flask into three flasks (described as a 1 to 3 split). In this manner, large numbers of flasks were generated for use in the in vitro assessment of osteoinductive potential of DMB. When these cells reached the confluent state (cells completely cover the available surface in the tissue culture flask occupied by the media) the media was changed to Dulbecco's Modified Eagles Medium (DMEM) supplemented with 2% FCS and bone powder (5 to 10 mg, FIG. 19) is added to each culture flask. As illustrated in FIG. 17, bone particles in the size range of 500 to 710µ provide for maximally induction of alkaline phosphatase in cultured human periosteal cells. The cells were cultured for 5 days in a 37° C. 5% $CO_2$ incubator and then assayed for levels of the enzyme alkaline phosphatase (FIG. 18). Over this incubation period, the cell numbers increased slightly, for example from approximately $1.4 \times 10^6$ cells/T-25 flask to $1.7 \times 10^6$ cells/T-25 flask. Alkaline phosphatase activity was measured by washing cells with deionized water (two times), scraping the cells from the flasks using a commercially available cell scraper (Fisherbrand) in 3 ml of deionized water. The cells were then sonicated at 30% intensity (Virsonic Cell Disrupter Model 16-850) for 30 seconds. One milliliter aliquots were mixed with 0.2 ml micromole/ml p-nitrophenyl phosphate in 0.15 M 20-amino-2-methyl-1-propanol buffer, pH 10.4, and incubated at 37° C. for 15 minutes. The reaction was stopped by addition of 50 microliters of 1 N NaOH and absorbance measured at 450 nm. Quantity of p-nitrophenol formed with time was calculated by comparing absorbance values against standard curves of absorbance versus concentration of authentic p-nitrophenol. Protein concentration were assayed using the BCA (Pierce Chemical Company) protein assays. Alkaline phosphatase activities were expressed as Units of Enzyme (micromoles p-nitrophenol/min/mg cell protein). Properly demineralized bone (DMB), i.e. bone demineralized to approximately 2% residual calcium (FIG. 22), is maximally active in inducing elevated levels of alkaline phosphatase in cultured human periosteal cells. As illustrated in FIG. 9, the in vitro and in vivo assays correlated in their predictive potential approximately 74% of the time.

EXAMPLE 4

Demineralization of Other Types of Bone

Cortical/cancellous bone strips/cubes are added to the tall inner vessel of the present controlled-flow apparatus in a mesh bag (for example, nylon) or similar device designed to prevent the bone from interfering with the stirring of the liquids being pumped into the demineralization apparatus. The apparatus is closed and hydrochloric acid, 0.5 N, is quickly pumped into the apparatus with stirring begun as soon as a sufficient volume of acid has been pumped into the chamber to permit free movement of the solution through the bone grafts present in the chamber. The pH of the eluent solution is monitored to determine the degree and extent of demineralization of the small bone grafts. Because these bone grafts have a larger volume to surface area than dental bone, the demineralization process takes longer and represents a compromise in average wt % residual calcium present throughout the bone graft being demineralized. The surfaces of these bone grafts are more extensively demineralized than the interiors of these bone grafts and thus the average wt % residual calcium desired must approximate 2.0% to 4.0% in order for the bone to be maximally osteoinductive in a clinical situation, eg. cortical bone allografts demineralized to an average wt % residual calcium of approximately 3.0% will approximate 1.5 to 2.0 wt % on the surface of the bone graft making the surface of the bone graft optimally osteoinductive. Following completion of the desired level of demineralization, the controlled-flow apparatus is immediately drained of acid through drain port 6 and the contents washed extensively with sterile endotoxin-free distilled/deionized water. The pH of the bone is then restored to approximate neutrality by pumping sodium/potassium phosphate buffer (0.01 M, pH 7.0–7.4) into the controlled-flow apparatus until the eluent solution is pH 7.0 to 7.4. The optimally demineralized cortical/cancellous bone may be stored under refrigeration until the osteoinductive potential of small aliquots have been evaluated.

The osteoinductive potential of these small aliquots of optimally demineralized bone may be assessed using the in vivo and/or in vitro assays described herein following fragmentation to particle sized approximating 500 to 710$\mu$.

If the cortical/cancellous bone grafts have not been sufficiently demineralized so as to be maximally osteoinductive, they may be returned to the controlled-flow apparatus for further demineralization with hydrochloric acid. If the cortical/cancellous bone grafts have been overly demineralized so as to be less than maximally osteoinductive, the bone grafts may be added to a solution of calcium phosphate, for example 2.0 to 0.1 M CaHPO4, at a pH of less than 2.5 and incubated for a period of time readily determined to be sufficient by one of ordinary skill in the art for the calcium phosphate solution to completely permeate the cortical/cancellous bone grafts. The time required for the calcium phosphatase to completely permeate the cortical/cancellous bone grafts can be calculated by those skilled in the art through use of diffusion coefficients for those ions based on their molecular weights, temperature, distance required for the ions to move in permeating the tissues, and nature of the viscosity of the solution(s). In general, diffusion rates for specific molecules are available in standard table such as in the CRC Chemical Handbook. Based on the tissues being permeated, permeation times would approximate only 3 to 5 minutes.

At that time, the pH of the calcium phosphate solution is increased by the addition of 1.0 to 5.0 N sodium hydroxide (NaOH) to a pH greater than 6.0 but less than 11.0. The calcium phosphate solution will form a fine precipitate at pH values greater than pH 6.0 causing the calcium phosphate to form various crystalline forms of calcium phosphate on and in the cortical/cancellous bone grafts. The concentration of calcium in an optimally demineralized and/or reconstituted bone graft can be ascertained using any of the commercially available calcium assay methods, for example atomic absorption, Arsenazo III (Sigma Chemical Company, St. Louis, Mo.), etc.

Following demineralization, the cortical/cancellous bone grafts may be further exposed to alcohols, for example 70% (vol:vol) isopropyl alcohol or ethanol, hydrogen peroxide, antibiotics, growth factors, cytokines, fibrins, antivirals, surfactants, softening agents, and the like with the objective that these further treatment regimes not reduce the osteoinductive potential of the derived bone graft. Exposure to these additional agents may be accomplished by pumping these solutions through the controlled-flow apparatus using the same pumping mechanism as used to deliver the hydrochloric acid used to demineralize the bone grafts.

EXAMPLE 5

Percent Residual Calcium in Demineralized Bone Versus Time of Exposure to the Demineralization Process To examine the relationship between wt % residual calcium in demineralized bone versus time of exposure of the bone to the demineralization process, 300 g wet weight of properly sized ground bone (250$\mu$ to 710$\mu$), and a stirbar were placed into the tall inner vessel of the present controlled-flow apparatus. The apparatus was closed and placed onto an external stirring drive. The apparatus was filled with 0.5 N hydrochloric acid and stirring was begun as soon sufficient fluid was present to permit suspension of the bone material. As soon as the apparatus was full, stirring in acid flow were adjusted to maintain the bone material in suspension. The initial pH of the eluent acid varied from run to run. In Run No. 1, the initial pH was 1.7, while in Run No. 2 the pH was 2.7 and in Run No. 3 the initial pH was 2.85. The pH of eluent acid was then measured every 7 minutes along with the removal of a bone sample. The demineralization process was stopped once the pH of the eluent acid solution reached about 1.0. As can be seen from the data, Run No. 1 was carried out for 322 minutes, Run No. 2 was carried out for 343 minutes, and Run No. 3 was carried out for 210 minutes.

Each bone sample to be assayed for wt % residual calcium, after removal from the present controlled-flow apparatus was washed sterile distilled/deionized endotoxin-free water. After sufficient washing occurred to raise pH of the bone material to greater to about pH 3.0, the pH of the bone material was increased to approximately pH 7.0.

The bone samples were then assayed for wt % residual calcium. The resultant data, as to the wt % residual calcium, was then plotted against the elapsed time of exposure to the demineralization process. As can be seen from FIGS. 23, 25, and 27, a linear relationship exists between elapsed time and wt % residual calcium. As can be seen from FIGS. 24, 26, and 28, a linear relationship exists between pH of the eluent solution and the wt % residual calcium in the bone at the time the pH was determined. The data is set forth below.

A. Run Number 1

| | Research Run #1 95-0767 Donor # | |
|---|---|---|
| Elapsed Time | % Calcium | pH |
| 0 | 23.2 | 1.7 |
| 7 | 23.9 | 2.43 |
| 14 | 23.4 | 2.47 |
| 21 | 22 | 2.5 |
| 28 | 22.6 | 2.3 |
| 35 | 22 | 2.38 |
| 42 | 22 | 2.44 |
| 49 | 21.8 | 2.53 |
| 56 | 23.1 | 2.58 |

-continued

Research Run #1
95-0767 Donor #

| Elapsed Time | % Calcium | pH |
|---|---|---|
| 63 | 21 | 2.64 |
| 70 | 19.8 | 2.58 |
| 77 | 20.3 | 2.48 |
| 84 | 18.9 | 2.6 |
| 91 | 19.7 | 2.62 |
| 98 | 19.7 | 2.55 |
| 105 | 18.7 | 2.56 |
| 112 | 18.9 | 2.53 |
| 119 | 18.8 | 2.6 |
| 126 | 18.2 | 2.58 |
| 133 | 17.9 | 2.57 |
| 140 | 24.2 | 2.55 |
| 147 | 17.3 | 2.35 |
| 154 | 17.7 | 2.33 |
| 161 | 16.2 | 2.26 |
| 168 | 14.8 | 2.2 |
| 175 | 14.5 | 2.14 |
| 182 | 14.1 | 1.94 |
| 189 | 13.4 | 2.06 |
| 196 | 12.7 | 1.99 |
| 203 | 11.5 | 2 |
| 210 | 12.1 | 1.88 |
| 217 | 12.3 | 1.86 |
| 224 | 12.1 | 1.81 |
| 231 | 9.6 | 1.76 |
| 238 | 9.4 | 1.69 |
| 245 | 8.4 | 1.65 |
| 252 | 10.3 | 1.58 |
| 259 | 9.8 | 1.58 |
| 266 | 8.2 | 1.46 |
| 273 | 9.6 | 1.45 |
| 280 | 7.7 | 1.37 |
| 287 | 6.7 | 1.32 |
| 294 | 3.9 | 1.21 |
| 301 | 2.3 | 1.15 |
| 308 | 1.5 | 1.06 |
| 315 | 0.8 | 1.04 |
| 322 | 0.1 | 0.97 |
| Correlation | 0.915137402 | |
| Prediction at 210 | | |

B. Run Number 2

Research Run #2
95-1338 Donor #

| Elapsed Time | % Calcium | pH |
|---|---|---|
| 0 | 27.5 | 2.17 |
| 7 | 27.5 | 3.14 |
| 14 | 27.9 | 2.66 |
| 21 | 27.4 | 2.51 |
| 28 | 23.9 | 2.62 |
| 35 | 24.2 | 2.4 |
| 42 | 24.4 | 2.43 |
| 49 | 27.4 | 2.47 |
| 56 | 23.5 | 2.49 |
| 63 | 23.1 | 2.46 |
| 70 | 22.7 | 2.3 |
| 77 | 23.5 | 2.28 |
| 84 | 22.5 | 2.03 |
| 91 | 21.5 | 2.03 |
| 98 | 23 | 2.02 |
| 105 | 23 | 2.1 |
| 112 | 23.5 | 2.2 |
| 119 | 22.5 | 2.03 |
| 126 | 21.9 | 2.08 |
| 133 | 17.9 | 2.11 |

-continued

Research Run #2
95-1338 Donor #

| Elapsed Time | % Calcium | pH |
|---|---|---|
| 140 | 20.5 | 2.09 |
| 147 | 24 | 2.07 |
| 154 | 22.3 | 2.06 |
| 161 | 21.1 | 2 |
| 168 | 21.2 | 2.1 |
| 175 | 19.8 | 1.98 |
| 182 | 20.5 | 2.07 |
| 189 | 21.1 | 2.07 |
| 196 | 21 | 1.89 |
| 203 | 22.6 | 2.06 |
| 210 | 18.8 | 1.95 |
| 217 | 16.3 | 1.89 |
| 224 | 16.5 | 1.83 |
| 231 | 14.6 | 1.82 |
| 238 | 14.4 | 1.78 |
| 245 | 13.5 | 1.74 |
| 252 | 13.1 | 1.67 |
| 259 | 13.1 | 1.62 |
| 266 | 10.9 | 1.58 |
| 273 | 9.7 | 1.54 |
| 280 | 10.3 | 1.5 |
| 287 | 7.2 | 1.43 |
| 294 | 8.2 | 1.43 |
| 301 | 7.7 | 1.36 |
| 308 | 7.8 | 1.33 |
| 315 | 6.2 | 1.29 |
| 322 | 3.8 | 1.25 |
| 329 | 4.6 | 1.2 |
| 336 | 3.1 | 1.11 |
| 343 | 3.1 | 1.03 |
| Correlation Coef. | 0.938211812 | |
| Prediction at 210 | 15.31460264 | |

C. Run Number 3

Research Run #3
95-0760 Donor #

| Sample | % Calcium | pH |
|---|---|---|
| 0 | 22.5 | 2.85 |
| 7 | 22.3 | 3 |
| 14 | 20.9 | 2.75 |
| 21 | 22.3 | 3 |
| 28 | 22.1 | 2.48 |
| 35 | 21.7 | 2.75 |
| 42 | 21 | 2.55 |
| 49 | 20.5 | 2.45 |
| 56 | 20.1 | 2.56 |
| 63 | 19.7 | 2.63 |
| 70 | 19.5 | 2.55 |
| 77 | 19.7 | 2.23 |
| 84 | 18.3 | 2.11 |
| 91 | 16.6 | 1.97 |
| 98 | 14 | 2 |
| 105 | 13.7 | 2.04 |
| 112 | 12 | 1.92 |
| 119 | 12.5 | 1.82 |
| 126 | 10.2 | 1.6 |
| 133 | 13.5 | 1.62 |
| 140 | 9.8 | 1.54 |
| 147 | 11.4 | 1.54 |
| 154 | 10.3 | 1.48 |
| 161 | 9 | 1.41 |
| 168 | 9.6 | 1.36 |
| 175 | 6.4 | 1.28 |
| 182 | 3.1 | 1.21 |

-continued

Research Run #3
95-0760 Donor #

| Sample | % Calcium | pH |
| --- | --- | --- |
| 189 | 3.4 | 1.12 |
| 196 | 1.8 | 1.08 |
| 203 | 2.3 | 1.04 |
| 210 | 1 | 0.99 |
| Correlation Coef. | 0.963641768 | |
| Pred. at 210 min. | 2.657258065 | |

EXAMPLE 6

Time Course of Implant Remineralization

DBM (20 mg) were implanted into muscle pouches and the implant were explanted at weeks 1, 2, 3, 4, and 5. Muscle and connective tissue around the explants were extensively cleaned. The explants were dried overnight at 90° C. and dry weights were obtained. The dried materials were then placed into crucibles and ashed in a furnace for 24 hours. The calcium content in each explant was measured and expressed as weight percent of the dry weight of explants. The data are expressed as mean±SE, n=3. The data illustrated in FIG. 14 shows that the implanted materials are remineralized in an approximately linear time dependent manner. In performing regression analyses, two linear relationships were noted, one between week 0 and week 3 and week 5, where the rate of remineralization after week 3 is greater than the rate of remineralization prior to week 3. Overall, the implanted DBM is remineralized in a nearly linear time dependent manner over the 5 weeks of the assay. Please see FIG. 14.

EXAMPLE 7

In Vivo Nude Mouse Assay

DBM (10, 20, 30, 40 mg) were implanted into muscle pouches, explanted after 4 weeks, and following explantation and cleaning as described in Example 6, analyzed for calcium content. Please see FIG. 15.

EXAMPLE 8

Explant Weight of 20 mg DBM Implanted after Four Weeks in the Nude Mouse

Bone particles were separated into specific size ranges based on the sizing characteristics of the seives used to separate the demineralized bone particles. 20 mg of each size range of bone particle were implanted into muscle poucher, explanted after 4 weeks and cleaned as described in Example 6. As can be seen in FIG. 16, small bone particle sizes are more readily resorbed in the muscle pouch of the nude mouse.

EXAMPLE 9

Time Course of Alkaline Phosphatase Induction in the Present In Vitro Assay in the Presence and Absence of Ground DBM HPO cells were seeded at $6.25 \times 10^3$ cells/T-25 tissue culture flask and grown to confluency in alpha-MEM supplemented with 10% fetal calf serum. The medium was then changed to DMEM supplemented with 2% fetal calf serum and bone (5 mg) was added. Alkaline phosphate activities were assayed daily and expressed as the mean±SE. At day 5, alkaline phosphatase activities were approximately 2–3 times higher in the bone treated as compared to the non-bone treated cells, describing the essential basis of the in vitro bioassay of demineralized bone for osteoinductive potential. See FIG. 18.

EXAMPLE 10

In Vitro Assay

Alkaline phosphate activities were analyzed using a commercially available kit from Sigma Chemical Company, St. Louis, Mo. DBM particles in the size range 500–700$\mu$ provided for significantly (p=0.05) elevated levels of alkaline phosphatase in the human periosteal cell line. See FIG. 17.

EXAMPLE 11

Dose Response Curve Describing the Increase in Alkaline Phosphatase Activity in the Human Periosteal Cells as a Function of the Amount Demineralized Bone Added to Cultured Cells HPO cells were seeded as in Example 9, into separate T-25 tissue flasks. A different amount of DBM was added to each flask. Alkaline phosphatase activity was assayed at day five. Amounts of DBM approximating 5 to 10 mg were clearly optimal. See FIG. 19.

EXAMPLE 12

Correlation of the Present In Vivo and In Vitro Assays

Linear regression analysis indicated a correlation ($R^2$) of 0.74, i.e. the two assays correlated approximately 74% of the time. See FIG. 20.

EXAMPLE 13

The Effect that % Residual Calcium in DBM has on Subsequent Remineralization Potential Following Implantation into the Nude Mouse Non-demineralized bone actually lost calcium over the assay interval and bone demineralized to approximately 2% residual calcium is clearly, significantly (p=0.05), optimally osteoinductive. See FIG. 21.

EXAMPLE 14

The Effect that Wt % Residual Calcium in DBM has on Subsequent Induction of Alkaline Phosphatase Following Addition to Confluent Cultures of Human Periosteal Cells Bone demineralized to approximately 2% residual calcium is clearly, significantly (p=0.05), optimally "osteoinductive" (assay does not actually measure osteoinductivity, but is expressed in this format to better illustrate the correlation with the in vivo assay). See FIG. 22.

All of the publications cited herein are hereby incorporated by reference into the present disclosure.

It will be appreciated by those skilled in the art that various modifications can be made without departing from the essential nature thereof. It is intended to encompass all such modifications within the scope of the appended claims.

What is claimed:

1. A process for producing osteoinductive bone, comprising the step of:
   contacting bone with an acid solvent under conditions effective to demineralize said bone to contain 1.8 wt % to 2.5 wt % residual calcium, wherein osteoinductive bone is produced.

2. The process of claim 1, wherein said step of contacting comprises:
   contacting said bone with a continuous flow of one or more acidic solvents.

3. The process of claim 1, wherein said step of contacting with acidic solvent is carried out for a time of from about 80 min. to about 200 min.

4. A process for producing osteoinductive bone demineralized to contain 1.8 wt % to 2.5 wt % residual calcium comprising the step of:
   contacting said bone with a flow of detergent solvent to produce bone substantially free from bone marrow elements;
   contacting said bone with a flow of acidic solvent under conditions effective to demineralize bone to contain 1.8 wt % to 2.5 wt % residual calcium, to produce osteoinductive bone.

5. The process of claim 4, further comprising the step of:
   dehydrating said osteoinductive bone.

6. The process of claim 5, wherein said dehydrating step comprises:
   contacting said osteoinductive bone with a flow of a dehydrating solvent.

7. The process of claim 6, wherein said dehydrating solvent comprises:
   one or more alcohols.

8. The process of claim 4, further comprising:
   periodically sampling pH of an eluent acidic solvent during said step of contacting said bone with a flow of acidic solvent until a pH of from about 0.8 to about 1.5 has been reached;
   washing said bone with water to produce osteoinductive bone.

9. A process for producing osteoinductive bone, comprising:
   contacting bone in a container, said container, comprising having an inlet and an outlet, with a flow of acid solvent wherein said acid solvent flows into said container through said inlet and eluent acid solvent exits said container through said outlet;
   periodically sampling pH of eluent acid solvent exiting container through said outlet, during said step of contacting until eluent acid solvent reaches a pH of from 0.8 to 1.5 to produce demineralized bone; and
   washing said demineralized bone with water to produce osteoinductive bone, wherein osteoinductive bone is produced.

10. The process of claim 9, wherein said bone comprises one or more members selected from the group consisting of:
    ground bone; cortical or cancellous bone strips; cortical or cancellous bone cubes; and cortical or cancellous bone chips.

11. The process of claim 9, wherein said step of contacting is carried out until said eluent acid solvent reaches a pH of from 0.9 to 1.2.

12. Osteoinductive bone produced by the process as claimed in any one of claims 9 or 11.

13. The process of claim 9, further comprising;
    prior to said step of contacting, subjecting said bone to a flow of detergent solution to remove bone marrow elements from said bone.

14. A method for producing osteoinductive bone from demineralized bone having less than 2.0 wt % residual calcium, comprising:
    suspending said demineralized bone in calcium phosphate at a pH of from 1.5 to 3.5 to produce a suspension;
    incubating said suspension to form an incubated suspension;
    adjusting pH of said incubated suspension to from 5.5 to 8.5 to produce adjusted suspension; and
    washing said adjusted suspension to produce osteoinductive bone, wherein osteoinductive bone is produced.

15. The method of claim 14, wherein said suspension is incubated for from about 2.5 to about 15 minutes.

16. Osteoinductive bone suitable for use in humans, comprising:
    bone demineralized to an extent that bone produced contains approximately 2.0 wt % to 2.2 wt % residual calcium.

17. The process of any one of claims 1, 9, 14, or 16, wherein said osteoinductive bone comprises human or animal bone.

* * * * *